| United States Patent [19] | [11] Patent Number: 4,976,770 |
| Barnes et al. | [45] Date of Patent: Dec. 11, 1990 |

[54] HERBICIDAL AND PLANT GROWTH REGULANT ACTIVITY OF GLYOXYLATES

[75] Inventors: Keith D. Barnes, Newtown; Frederick W. Hotzman, Morrisville, both of Pa.; Lawrence E. Limpel, Euclid; Thomas A. Magee, Mentor, both of Ohio

[73] Assignee: Fermenta ASC Corporation, Mentor, Ohio

[21] Appl. No.: 373,210

[22] Filed: Jun. 29, 1989

[51] Int. Cl.$^5$ ............................................. A01N 43/24
[52] U.S. Cl. ....................................... 71/88; 549/267; 549/349
[58] Field of Search ..................... 71/88; 549/349, 267

[56] References Cited

U.S. PATENT DOCUMENTS 3,553,234  1/1971  Johnson et al. ..................... 549/349
3,836,543  9/1974  Grisar ................................. 549/349

Primary Examiner—Glennon H. Hollrah
Assistant Examiner—Amelia A. Owens
Attorney, Agent, or Firm—Fay, Sharpe, Beall, Fagan, Minnich & McKee

[57] ABSTRACT

12H-dibenzo[d,g][1,3]dioxocin-6-carboxylic acid and certain derivatives thereof (glyoxylates) exhibit plant growth regulant and herbicidal activity when applied to a plant locus.

5 Claims, No Drawings

HERBICIDAL AND PLANT GROWTH REGULANT ACTIVITY OF GLYOXYLATES

BACKGROUND OF THE INVENTION

The invention relates broadly to 12H-dibenzo[d,g][1,3]dioxocin-6-carboxylic acid and certain derivatives thereof, generally referred to herein as "glyoxylates", and their use as plant growth regulant and/or herbicidal agents and more particularly to their use, usually in combination with appropriate carriers and surfactants, in influencing the growth and development of crops, ornamentals and turf grasses.

The compounds which find utility in the present invention are known generically, and specifically in the case of the methyl ester, from U.S. Pat. No. 3,553,234. Therein, a class of compounds described as 12H-dibenzo[d,g][1,3]dioxocin-6-carboxylic acids and their esters and having the formula

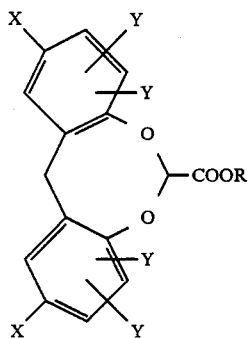

wherein X and Y are hydrogen or a halogen and R is hydrogen or lower alkyl is disclosed to have utility as hypolipidemic agents for warm blooded animals. Also mentioned are the pharmaceutically acceptable salts of such acids. However, no utility in the agricultural field is suggested.

The present invention is based upon the discovery that a selected group of such compounds possesses unexpected activity when employed as plant growth regulant and/or herbicidal agents at controlled dosages, while other closely related compounds within the genus of U.S. Pat. No. 3,553,234 display no significant agrochemical activity.

SUMMARY OF THE INVENTION

There has now been discovered a method of modifying the natural growth and development of a plant, which method comprises applying to the plant locus an effective, non-lethal, plant regulating amount of a compound having the formula

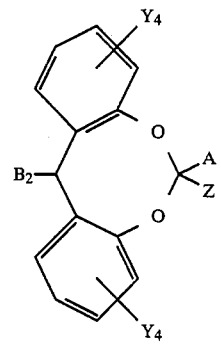

wherein:

A is COOR, COSR, CSNH$_2$, CN or, together with one of B, —C(=O)0—

R is H, Na, K, di(C$_1$-C$_4$)alkylammonium, diethanolammonium, C$_1$-C$_8$ alkyl, C$_1$-C$_4$ alkoxyalkyl, cyclohexyl, tetrahydrofurfuryl or dimethyldioxolanylmethyl;

Z is H or CH$_3$;

B is H, CH$_3$ or, together with A, —C(=O)0—;

Y is H, C$_1$-C$_4$ alkyl or alkoxy, CF or X; and

X is F, Cl or Br, provided that where more than one of Y is other than H on either ring they must be in the 3, 4, 8 and/or 9 positions and, where Y is in the 1, 2, 10 or 11 positions on the rings, no more than one of Y is other than H and that one Y is CH$_3$. In other embodiments, no more than one of Y is other than H on either ring.

There has further been found a method of controlling the growth of undesired vegetation, which method comprises applying to the vegetation locus, especially by postemergent application, a herbicidally effective amount of a compound having the same formula as above.

There has still further been found a composition of matter useful in the regulation of plant growth and development, which composition comprises a compound having the same formula as above, an inert carrier and a surfactant.

In a preferred embodiment of the foregoing methods and composition of the present invention, Y, B and Z are all H, resulting in a compound having the formula

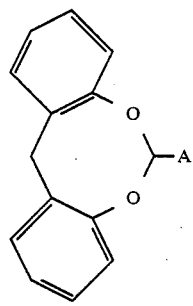

In a further embodiment of the foregoing methods and composition of the present invention, B and Z are all H, resulting in a compound having the formula

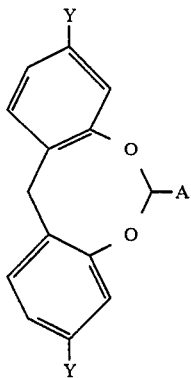

In yet another embodiment of the foregoing methods and compositions, Y and Z are all H, resulting in a compound the formula

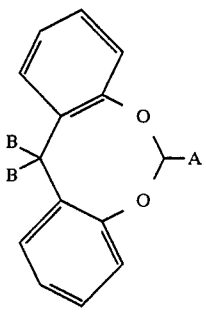

The invention also encompases certain novel compounds having herbicidal and/or plant growth regulating activity having the formula

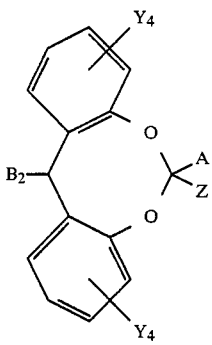

wherein:
A is COOR, COSR, CSNH$_2$, CN or, together with one of B, —C(=O)O—;
R is C$_1$-C$_4$ alkoxyalkyl, cyclohexyl, tetrahydrofurfuryl and dimethyldioxolanylmethyl;
Z is H or CH$_3$;
B is H, CH$_3$ or, together with A, —C(=O)O—;
Y is H, C$_1$-C$_4$ alkyl or alkoxy, CF$_3$ or X; and X is F, Cl or Br,
provided that where more than one of Y is other than H on either ring they must be in the 3, 4, 8 and/or 9 positions and, where Y is in the 1, 2, 10 or 11 positions on the rings, no more than one of Y is other than H and that one Y is CH$_3$. In other embodiments, no more than one of Y is other than H on either ring.

Another group of novel compounds within the scope of the invention has the formula

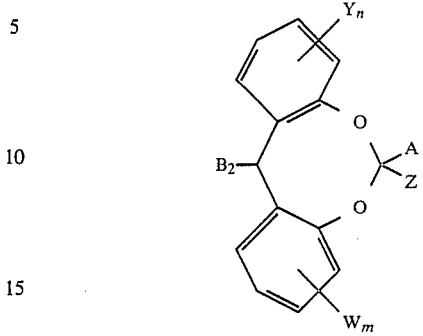

wherein:
A is COOR, COSR, CSNH$_2$, CN or, together with one of B, —C(=O)O—
R is H, Na, K, di(C$_1$-C$_4$)ammonium, diethanolammonium, C$_1$-C$_8$ alkyl, C$_1$-C$_4$ alkoxyalkyl, cyclohexyl, tetrahydrofurfuryl or dimethyldioxolanylmethyl;
Z is H or CH$_3$;
B is H, CH$_3$ or, together with A, —C(=O)O—;
Y and W are C$_1$-C$_4$ alkyl or alkoxy or CF$_3$;
m and n are 0–2 and the sum of m plus n is 1–4.

These and other aspects of the invention will become clear to one skilled in the art from the specification and claims that follow.

DETAILED DESCRIPTION

When used in the present invention, the terms "plant growth regulant" or "plant growth regulating effect" refer to the ability of a glyoxylate, when applied to a plant locus, to influence the growth and development of useful crops, ornamentals and turf A variety of effects may be obtained depending upon, among other considerations, the plant in question, the glyoxylate selected and the manner, amount and timing of application Generally the result obtained by application of a glyoxylate is the desirable promotion, inhibition and/or alteration of a plant's physiological or morphological processes, such as accelerating or retarding leaf, shoot and root growth, reduction in stature, increased branching, tillering, terminal inhibition, inhibition of regrowth after pruning thereby reducing the need for followup pruning, increased root growth, delayed budding, increased bud count, yield increases, etc. In particular, the glyoxylates of the present invention have been found to be effective growth retardants when applied to turf grasses such as, perennial rye, red and tall fescue and Kentucky bluegrass. A further example of a plant growth regulating effect is the ability of a glyoxylate compound, when timely applied (preferably in the second or third growth stage) to act as a straw shortening agent on wheat, an especially useful effect where high nutrient levels are employed to increase grain yield.

The use of the terms "herbicide" or "herbicidal effect" refers to the application of a glyoxylate compound to kill, or at least substantially inhibit the growth of, an undesired plant. Especially significant examples are the use of one of the glyoxylates to control the growth of weeds, including grassy weeds, in wheat and reduce flowering in bolting weed beets The glyoxylates have been found to be particularly useful in controlling the growth of the generally hard to control sedges, especially yellow nut sedge, when applied to the soil in which the nut sedge tubers are beginning to germinate.

The compounds useful herein are those having the formula

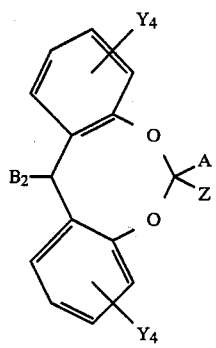

Each of the defined glyoxylate compounds has been found to have a herbicidal and/or plant growth regulating effect. In addition to activity and selectivity considerations, a particular ester or salt form of a glyoxylate will often be chosen for its convenience of handling and application, an example being the choice of the n-butyl ester, which has reduced volatility, over the methyl ester form. On the other hand, where volatility is desirable, e.g., for application by fumigation (smoke bombs) in a greenhouse to induce branching of ornamentals, compounds such as the nitrile and lower esters (e.g., methyl, ethyl and propyl) which are more volatile, may be preferred.

The choice of substituents to be placed on the benzene rings, on the other hand, seems to affect the nature and extent of plant growth regulating effect to be obtained and such subsitution is limited with respect to (1) the identity of the substituent, (2) location on the ring or rings and (3) number of substitutions that may be accommodated. Substitution opportunities are particularly limited when placed in the 1, 2, 10 and 11 positions according to the following number system:

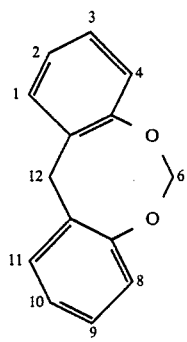

In such cases, substitution of a methyl group at no more than one position has been found possible without a significant loss of activity Substituent possibilities at the remaining benzene ring positions (3, 4, 8 and 9), in order to vary the growth regulating and/or herbicidal effect obtained without significant overall loss of activity, are more numerous. While it is preferred that not more than one position on either ring be substituted, the choice of substituents may be increased as defined above.

Generally the glyoxylates will be applied to the plant locus as the active ingredient in a composition also comprising a carrier and a surfactant, that is, a dispersing, emulsifying or wetting agent, although diluents, extenders and other active ingredients having a differing or complementary utility may be present The compositions may thus be in the form of finely divided particulate solids, granules, wettable powders, solutions and dispersions.

The inert carrier may be solid (e.g., clays, natural or synthetic silicates, talcs) or liquid (e.g., water, alcohols, esters, aromatic hydrocarbons, petroleum fractions). The surface active agents may be anionic, cationic or nonionic (e.g., salts of lignosulfonic acids, alkyl-aryl sulfonic acids, acetates of alkylamines and condensates of ethylene oxide with fatty alcohols or acids). In addition, the compositions may contain thickeners, adhesives, stabilizers, preservatives and other adjuvants known to the art.

The glyoxylates may be applied by conventional techniques (e.g., spreading, dusting or spraying or via fumigation smoke bombs in confined areas such as greenhouses) in a variety of forms (e.g., solutions, suspensions, wettable powders or granules).

The compositions of the present invention generally will contain from 5 to 95 percent by weight of the active glyoxylate compound and will be applied at a rate of from 0.5 to 4 kilograms per hectare, when used as herbicides. While in a plant growth regulating composition the amount of active ingredient may be comparable, the amount employed will vary greatly depending upon the particular glyoxylate chosen and the effect in question, generally ranging from 0.01 gram to 4 kg per hectare. Conveniently, such applications are obtained by spraying a solution containing from 0.1 to 500 ppm active ingredient to run-off, depending on the plant species to be treated.

The carboxylate compounds which are the subject of the present invention are derived from the acid form which may be prepared by methods known to the art, for example, according to the teachings of U.S. Pat. No. 3,836,543 incorporated herein by reference. Modifications and variations of these procedures where benzene ring substituents are other than those described in the '543 patent and where substitution is desired at the 12 position, are shown in the examples below. Thereafter, they may be converted to the final form generally according to methods also known in the art, for example, conventional esterification when preparing a lower alkyl ester.

In order that those skilled in the art may more readily understand the present invention and certain preferred embodiments by which it may be carried into effect, the following specific examples are afforded.

PREPARATIONS

EXAMPLE 1

12H-Dibenzo[d,g][1,3]dioxocin-6-carboxylic acid

Into a 12 liter 3-neck flask fitted with an air-driven overhead stirrer and a condenser are placed 2,2'-methylene bisphenol (200 24 gram, 1.0 mol), 4 liter of isopropyl alcohol and then potassium carbonate (552.84 gram, 4.0 mol), while stirring. Dichloroacetic acid, (82.5 ml, 1.0 mol) is added over a period of 2 minutes. During the addition of the dichloroacetic acid some effervescence is observed. The reaction mixture, which is a white, easily stirred, heterogenous mixture, is heated at reflux and stirred vigorously. After 24 hours, the reaction mixture is cooled to room temperature and an additional 82.5 ml (1.0 mol) of dichloroacetic acid is added. Again, some effervescence is observed The reaction mixture is then heated at reflux for an additional 72 hours. Total reflux time is 96 hours. After 48 hours of total reflux time, the reaction mixture thickens and vigorous stirring is maintained.

Once the 96hour reflux period is complete, the condenser is replaced with a distillation head and 200 ml of isopropyl alcohol is distilled off at atmospheric pressure and replaced with 200 ml of $H_2O$. This is repeated until the distillation termperature reaches 95°–100° C. During the distillation procedure, once $H_2O$ is added, the reaction mixture becomes much more fluid and eventually a reddish brown homogenous solution is obtained. After the distillation temperature reaches 95°–100° C., the reaction mixture is cooled to room temperature. Upon cooling, solids form, therefore it is important to maintain vigorous stirring. The reaction mixture is then made strongly acidic by the careful addition of concentrated HCl (800 ml) over a period of 1–2 hours. Extreme caution must be taken during the addition of the HCl because of effervescence. The effervescence is particularly vigorous during the latter stage of HCl addition Once the HCl has been added, the reaction is stirred an additional 2 hours at room temperature. The solids are collected by filtration and washed well with $H_2O$.

These solids are then placed in a separatory funnel with 2 liters of ethyl acetate and 2 liters of 1N HCl and shaken vigorously. The organic layer is separated, washed with brine, dried over $MgSO_4$ and concentrated. The solids obtained are then dried in a vacuum oven to afford 239 grams (93 percent) of crude product as a brown-tan solid, which are then placed in a Soxhlet extraction apparatus and exhaustively extracted with refluxing cyclohexane (2 liters). Periodically the cyclohexane solution is cooled and the precipitated product collected by filtration. The rate of the extraction depends on how vigorously the cyclohexane refluxes and recycles There is obtained 147 grams of 12H-dibenzo[d,g][1,3]dioxocin-6-carboxylic acid as a white solid: mp 153°–157° C.; IR (KBr) 5.78, 6.76, 6.93, 8.12, 10.1, 13.1 cm$^{-1}$; $^1$H NMR (60 MHz, DMSO-d$_6$) δ 3.64 and 4.38 (2d, 2, $CH_2$), 5.09 (s, 1, CH), 6.9–7.6 (m, 8, Ar—H); greater than 99 percent purity as determined by liquid chromatography.

EXAMPLE 2 n-Butyl 12H-Dibenzo[d,g][1,3]dioxocin-6-carboxylate

Into a 500 ml round bottom flask fitted with a stir bar and a Dean-Stark apparatus is placed 111.4 grams of crude (87 percent) 12H-dibenzo[d,g][1,3]dioxocin-6-carboxylic acid in 300 ml of 2:1 n-butanol:toluene. The mixture is stirred at room temperature for 15 minutes to effect the complete dissolution of the acid. Concentrated sulfuric acid (4.0 ml) is then added and the reaction mixture is heated to reflux Immediately upon attaining reflux, an aqueous layer begins to separate out in the Dean-Stark apparatus. After 2 hours at reflux, no additional water formation is observed and the reaction is cooled to room temperature with a cold water bath. A total of 10 ml of water is collected, the majority of this water being formed in the initial 30 minutes of reflux. The cooled reddish-yellow reaction solution is diluted with 200 ml of toluene, washed with 300 ml of water, 300 ml of saturated aqueous $NaHCO_3$, ml of brine and then concentrated under reduced pressure on a rota-vap. Toluene (200 ml) is added to the residue and the solution again is concentrated under reduced pressure This evaporation with toluene facilitates the removal of n-butanol. The residue obtained is taken up into 300 ml of 2:1 toluene:ether and washed with 200 ml of 5 percent NaOH. Brine, 50 ml, is added to break up the emulsion that forms with the 5 percent NaOH wash. The organic solution is then washed with 200 ml of brine, dried over $MgSO_4$ and concentrated under reduced pressure to afford a thick light reddish-yellow liquid (130 grams). This liquid is then subjected to vacuum distillation, using a Claisen adapter as the distillation head and an oil bath for heating. Care is taken during the course of the distillation to avoid solidification of the product in the distillation condenser. A forerun (11 grams) is collected having a b.p. 70° C. to 170° C. at 0.25 mm. Pure n-butyl ester, 84.3 grams (62 percent), is then collected from 171° C. to 180° C. at 0.25 mm as a thick clear liquid which readily solidifies on cooling to afford a white solid: mp 63°–66° C. (softening at 60° C.); greater than 99 percent purity as determined by L.C. bp 189°–195° C./0.4mm; IR (neat) 3.45, 5.75, 6.95, 8.35, 10.4 cm$^{-1}$; H NRM (60 MHz, CDCl$_3$) δ 0.9–1.9 (m, 7, OCH$_2$CH$_2$CH$_2$CH$_3$), 3.42 and 4.6 (2d, 2, $CH_2$), 4.35, (t, 2, OCH$_2$CH$_2$CH$_2$CH$_3$), 5.05 (s, 1, CH), 7.0–7.4 (m, 8, Ar—H)).

Anal. Calcd. for $C_{19}H_{20}O_4$: C, 73.06; H, 6.45 Found: C, 73.0; H, 6.7

EXAMPLE 3

Ethyl 12H-Dibenzo[d,g][1,3]dioxocin-6-carboxylate

A solution of 12H-dibenzo[d,g][1,3]dioxocin-6-carboxylic acid (31.8 grams, 0.124 mol) and conc. $H_2SO_4$ (1.6 ml) in 215 ml of ethanol is heated at reflux, allowing the condensate to pass through 4A molecular sieves After 2 hours, the reaction is cooled to room temperature and 100 ml of methylene chloride is added and then neutralized by the addition of solid $Na_2CO_3$. The salts are removed by filtration and the filtrate concentrated. The residue is taken up into $CH_2Cl_2$, washed with water, 5 percent aq. NaOH and brine, dried over $MgSO_2$ and concentrated to afford 31.1 grams (88 percent) of product as a white solid: mp 86.5°–88.5° C.; IR (KBr) 5.63, 6.7, 6.88, 7.2, 8.12, 8.98, 9.25, 10.1 cm.$^{-1}$; $^1$H NMR (60 MHz, CDCl$_3$) δ 1.4 (t, 3, CH$_3$), 3.43 and 4.6 (2d, 2, CH$_2$), 4.42 (q, 2, $CH_2$CH$_3$), 5.1 (s, 1, CH), 7.0–7.4 (m, 8, Ar—H).

Anal. Calcd. for $C_{17}H_{16}O_4$: C, 71.82; H, 5 67 Found: C, 71.7; H, 5.8

EXAMPLE 4

Methyl 12H-Dibenzo[d,g][1,3]dioxocin-6-carboxylate

Preparation proceeds as described in Example 3, only substituting methanol for ethanol Obtained is a white solid: mp 107°–110° C.; IR (KBr) 5.69, 6.77, 8.2, 9.3, 10.05 cm$^{-1}$; $^1$H NMR (60 MHz, CDCl$_3$) δ 3.5 and 4.62 (2d, 2, CH$_2$), 3.98 (s, 3, CH$_3$), 5.1 (s, 1, CH), 7.0–7.5 (m, 8, Ar—H).

Anal. Calcd. for $C_{16}H_{14}O_4$: C, 71.10; H, 5.22 Found: C, 71.0; H, 5.1

EXAMPLE 5 n-Propyl 12H-Dibenzo[d,g][1,3]dioxocin-6-carboxylate

Preparation proceeds as in Example 3, only substituting a like quantity of n-propanol for the ethanol, to obtain a white solid: mp 82°–85° C.; IR (KBr) 5.7, 8.35, 9.4, 10.15 cm$^{-1}$; $^1$H NMR (60 MHz, CDCl$_3$) δ 1.05 (t, 3, $CH_3$), 1.95 (m, 2, $CH_2CH_3$), 3.47 and 4.65 (2d, 2, $CH_2$), 4.33 (t, $CH_2CH_2CH_3$), 5.1 (s, 1, CH), 6.9–7.5 (m, 8, Ar—H).

Anal. Calcd. for $C_{18}H_{18}O_4$: C, 72.47; H, 6.08 Found: C, 72.7; H, 6.0

EXAMPLE 6 iso-Propyl 12H-Dibenzo[d,g][1,3]dioxocin-6-carboxylate

The subject product is prepared as described in Example 3, only substituting iso-propanol for ethanol, yielding a white solid: mp 94°–97° C.; IR (KBr) 5.73, 6.78, 8.25, 9.05, 9.4, 10.1 cm$^{-1}$; $^1$H NMR (60 MHz, $CDCl_3$) δ 1.4 (d, 6, CH—($CH_3$)$_2$), 3.46 and 4.6 (2d, 2, $CH_2$), 5.03 (s, 1,0—CH—O), 5.25 (m, 1, $CH(CH_3)_2$), 6.9–7.5 (m, 8, Ar—H)

Anal. Calcd. for $C_{18}H_{18}O_4$: C, 72.47; H, 6.08 Found: C, 72.4; H, 5.9

EXAMPLE 7 t-Butyl 12H-Dibenzo[d,g][1,3]dioxocin-6-carboxylate

A solution of 12H-dibenzo[d,g][1,3]dioxocin-6carboxylic acid (3.0 g, 0.0117 mol) in 45 ml of thionyl chloride is heated at reflux. After 4 hours at reflux, the excess thionyl chloride is distilled off at atmospheric pressure and then under vacuum to remove traces of thionyl chloride. The acid chloride obtained is dissolved in 35 ml of toluene and added dropwise over a period of 20 minutes to a solution of t-butyl alcohol (15 ml) containing N,N-dimethylaniline (1.8 ml, 0.01405 mol). After stirring 23 hours at room temperature, the reaction mixture is concentrated under reduced pressure and the residue obtained is taken up into ethyl acetate, washed with water and brine, dried over $MgSO_4$ and concentrated to yield 3.4 g of a syrupy residue. Dry column chromatography (elution with 1:4 ethyl acetate-hexanes) afforded 1.57 g (43 percent) of product as a white solid: mp 94°–97° C.; IR (KBr) 5.75, 8.22, 8.7, 9.43, 10.22, 13.21 cm$^{-1}$; $^1$H NMR (60 MHz, $CDCl_3$) δ 1.6 (s, 9, $C(CH_3)_3$), 3.45 and 4.6 (2d, 2, $CH_2$), 4.93 (s, 1, CH) 6.95–7.4 (m, 8, Ar—H).

Anal. Calcd. for $C_{19}H_{20}O_4$: C, 73.06; H, 6.45 Found: C, 73.0; H, 6.3

EXAMPLE 8 n-Octyl 12H-Dibenzo[d,q][1,3]dioxocin-6-carboxylate

12H-Dibenzo[d,g][1,3]dioxocin-6-carboxylic acid (4.0 g, 0.0156 mol) and 45 ml of thionyl chloride are refluxed/distilled as in Example 7. The acid chloride is then dissolved in 50 ml of toluene and added dropwise over a period of 10 minutes to a solution of n-octyl alcohol (20 ml) containing triethylamine (2.0 ml, 0.0187 mol). After stirring 20 hours at room temperature, the insolubles that form are filtered off and the filtrate concentrated under reduced pressure. The residue obtained is taken up into $CHCl_3$, washed with $H_2O$ then brine, dried over $MgSO_4$ and concentrated. The residue obtained is purified by dry column chromatography (elution with 1:10 ether-petroleum ether) to afford 4.18 g (73 percent) of product as a clear syrup; IR (neat) 3.42, 5.63, 6.71, 6.87, 8.95, 10.1 cm$^{-1}$; $^1$H NMR (60 MHz, $CDCl_3$) δ 0.9–2.0 (m, 15, $OCH_2$ $(CH_2)_6(CH_3)$), 3.48 and 4.62 (2d, 2, $CH_2$), 4.35 (t, 3, $OCH_2$ $(CH_2)_6CH_3$)), 5.07 (s, 1, CH), 7.0–7.5 (m, 8, Ar—H).

Anal. Calcd. for $C_{23}H_{28}O_4$: C, 74.97; H, 7.66 Found: C, 74.6; H, 8.2

EXAMPLE 9 n-Butoxyethyl 12H-Dibenzo[d,g][1,3]dioxocin-6-carboxylate

Crude 12H-dibenzo[d,g][1,3]dioxocin-6-carbonyl chloride (4.8 g, 17.5 mmol) is dissolved in toluene and treated with a solution of 2-butoxyethanol (2.77 ml, 21 mmol) and 5 ml of triethylamine in toluene at 0° C. under argon. The mixture is heated at reflux for 2 hours and then cooled to room temperature The mixture is poured into 150 ml of water and extracted with 4×100 ml of ethyl acetate. The organic solution is washed with 5 percent hydrochloric acid, 5 percent sodium hydroxide and then brine, dried with magnesium sulfate and filtered. The solvent is removed to leave a yellow liquid which is chromatographed on dry column silica gel, using ethyl ether/hexane (1:2) as the solvent, to give a yellowish oil (4.3 g, 69 percent) An analytically pure material is obtained by using prep thin layer chromatography. IR (neat) 1770, 1582 cm$^{-1}$. $^1$H NMR ($CDCl_3$) δ 0.75–1.3 (m, 3H, $CH_3$), 1.2–2.0 (m, 4H, $CH_2$), 3.3–4.0 (m, 5H, $OCH_2$and benzylic), 4.4–4.9 (m, 3H, $OCOCH_2$ and benzylic), 5.6 (s, 1H, CH), 6.9–7.5 (m, 8H, aromatic).

Anal. Calcd. for $C_{21}H_{24}O_5$: C, 70.7; H, 6.79 Found: C, 70.4; H, 6.9

EXAMPLE 10

Cyclohexyl 12H-Dibenzo[d,g][1,3]dioxocin-6-carboxylate

Crude 12H-dibenzo[d,g][1,3]dioxocin-6-carbonyl chloride (4 g, 14.5 mmol) is dissolved in 45 ml of toluene and treated with cyclohexanol (1.75 g, 17.5 mmol) and 3 ml of triethylamine at 0° C. under argon. The mixture is heated at reflux for 2 hours, cooled, washed with 5 percent sodium hydroxide then brine, dried with magnesium sulfate and filtered. The solvent is removed to leave a brown liquid which is chromatographed on dry column silica gel, using ethyl ether/hexane as solvent, to isolate a yellow solid. This solid is decolorized with charcoal to give a off-white solid (4.32 g, 87.7 percent), mp 120°–125° C.: IR (KBr) 1755, 1580 cm$^{-1}$. $^1$H NMR ($CDCl_3$) δ 1.0–2.4 (m, 11H, cyclohexyl), 3.37, 3.6, 4.51 and 4.73 (q, 2H, $CH_2$), 5.05 (s, 1H, OCH) 6.9–7.45 (m, 8H, aromatic).

Anal. Calcd. for $C_{21}H_{22}O_4$: C, 74.54; H, 6.55 Found: C, 74.3; H, 6.6

EXAMPLE 11

Tetrahydrofurfuryl 12H-Dibenzo[d,g][1,3]dioxocin-6-carboxylate

To a solution of crude 12H-dibenzo[d,g][1,3]dioxocin-6-carbonyl chloride (4.25 g, 15 mmol) in toluene is slowly added a solution of tetrahydrofurfuryl alcohol (1.8 ml, 18 mmol) and 3 ml of triethylamine in toluene at 0° C. under nitrogen The mixture is heated at reflux for 1 hour, cooled and treated with water and ethyl acetate. The organic layer is washed with 10 percent sodium hydroxide then brine, dried with magnesium sulfate and filtered. The solvent is removed leaving a yellowish oil which is chromatographed on dry column silica gel using ethyl acetate/hexane as the solvent. The resultant (still yellow) oil is decolorized with charcoal and solidified to yield a white solid (4.12 g, 78 percent) mp 83°–85° C. IR (KBr) 1760, 1580, cm$^{-1}$, $^1$H NMR ($CDCl_3$) δ 1.6–2.4 (m, 4H, $CH_2$), 3.35, 3.57, 4.5 and 4.71

(q, 2H, CH$_2$), 3.7-4.1 (m, 2H, CH$_2$O ), 4.1-4.5 (m, 3H, OCH$_2$CHO), 5.1 (S, 1H, CH) 6.95-7.5 (m, 8H, aromatic).

Anal. Calcd. for C$_{20}$H$_{20}$O$_5$: C, 70.58; H, 5.92 Found: C, 70.8; H, 5.9

EXAMPLE 12

Ethyl 12H-Dibenzo[d,q][1,3]dioxocin-6-thiocarboxylate

To a solution of 12H-dibenzo[d,g][1,3]dioxocin-6-carboxylic acid (1 gram, 3.9 mmol) and ethanethiol (0.8 ml, 5.9 mmol) in 10 ml of dry tetrahydrofuran at −25° C., is added dicyclohexyl carboximide (DCC, 2 grams, 9.8 mmol) under argon. The mixture is stirred at −20° C. for 2 hours and then kept in the refrigerator overnight. The mixture is warmed to room temperature and to it is added an aqueous solution of oxalic acid to destroy the excess DCC. The mixture is diluted with ethyl ether and filtered. The solid is washed with ethylacetate and the filtrate separated. The organic layer is washed with 10 percent sodium hydroxide and then with water twice and brine once the organic solution is next dried over magnesium sulfate and filtered. The solvent is removed to give a yellowish viscous oil which was chromatographed on dry column silica gel using ethyl acetate/-hexane (1:2) as the solvent to give a yellowish viscous oil (890 mg). This oil was solidified in petroleum ether to give a white solid, mp 77.5°-79° C.: IR (KBr) 1690, 1000, 7580 cm$^{-1}$; $^1$H NMR (CDCl$_3$) δ 1.2-1.6 (t, 3H, CH$_3$), 2.82-3.28 (q, 2H, SCH$_2$), 3.37, 3.58, 4.49 and 4.69 (q, 2H CH$_2$), 4.99 (s, 1H, CHO), 7.02-7.45 (m, 8H, aromatic).

Anal. Calcd. for C$_{17}$H$_{16}$O$_3$S: C, 67.98; H, 5.37 Found: C, 67.8; H, 5.5

EXAMPLE 12A

12H-Dibenzo[d,g][1,3]dioxocin-6-thiocarboxamide

A stirred solution of 12H-dibenzo[d,g][1 3]dioxocin-6-carboxamide (3.88 grams, 0.0152 mol) and Lawesson's reagent (3.69 grams, 0.00912 mol) in 40 ml of toluene is heated at reflux. After 2 5 hours, the reaction is cooled to room temperature and concentrated under reduced pressure to afford a dark gummy residue Flash chromatography of this material (elution with CH$_2$Cl$_2$) affords 1.6 grams of product as a tan solid. Recrystallization from hexanes results in 1.1 grams of product as an off white solid: mp 165°-169° C.; IR (KBr) 3380, 3140, 1615, 1440, 1220, 975 cm$^{-1}$; $^1$H NMR (DMSO-d$_6$) δ 3.65 and 4.41 (2d, 2, 12a and 12b), 5.17 (s, 1, H$_6$), 7.0-7.6 (m, 8, Ar—H).

Anal. Calcd. for C$_{15}$H$_{13}$NO$_2$S: C, 66.4; H, 4.8; N, 5.2 Found: C, 66 5; H, 4.9; N, 5.1

EXAMPLE 13

12H-Dibenzo[d,g][1,3]dioxocin-6-nitrile

To a stirred solution of 12H-dibenzo[d,g][1,3]dioxocin-6-carboxamide (8.24 grams, 0.0323 mol) and pyridine (5.74 ml, 0.071 mol) in 80 ml of 1,4-dioxane at 0° C., is added trifluoroacetic anhydride (5.0 ml, 0.0355 mol). After stirring for 5 minutes at 0° C., the reaction is warmed to room temperature and stirred for 3 hours. The volatiles are removed under reduced pressure, the residue taken up into ethyl acetate, washed with IN HCl, H$_2$O saturated aqueous NaHCO$_3$, brine, dried over MgSO$_4$ and concentrated to afford 6.8 grams of a white solid. Recrystallization from cyclohexane affords 5.46 grams (71 percent) of product as a white solid; mp 127°-130° C.; IR (KBr) 6.28, 6.71, 6.85, 7.44, 8.1, 8.45, 8.96, 13.1 cm$^{-1}$; $^1$H NMR (60 MHz, CDCl$_3$) δ 3.83 and 4.29 (2d, 2, CH$_2$), 5.84 (s, 1, CH), 7.2-7.0 (m, 8, Ar—H).

Anal. Calcd. for C$_{15}$H$_1$NO$_2$: C, 75.94; H, 4.07; N, 5.90 Found: C, 75.8; H, 4.0; N, 5.9

EXAMPLE 14

Sodium 12H-Dibenzo[d,g][1,3]dioxocin-6-carboxylate

A solution of 12H-dibenzo[d,g][1,3]dioxocin-6-carboxylic acid (1.3 grams, 0.00507 mol) and NaOH (0.41 grams, 0.0101 mol) in 50 ml of methanol is refluxed for 30 minutes. The reaction mixture is then concentrated under reduced pressure and the residue recrystallized from ethanol-water to afford 0.65 grams (45 percent) of product as a white solid: mp greater than 320° C; IR (KBr) 3.0, 6.2, 7.0, 8.25, 8.35, 10.45, 13.3 cm$^{-1}$; $^1$H NMR (60 MHz, D$_2$O ) δ 3.3 and 4.4 (2d, 2, CH$_2$), 4.8 (s, 1, CH), 6.8-7.4 (M, 8, Ar—H).

Anal. Calcd. for C$_{15}$H$_{11}$O$_4$Na 1/2 H$_2$O: C, 62.7; H, 4.2 Found: C, 63.0; H, 3.9

EXAMPLE 15

Potassium 12H-Dibenzo[d,g][1,3]dioxocin-6-carboxylate

A mixture of 12H-dibenzo[d,g][1,3]dioxocin-6-carboxylic acid (5.0 g, 0.0195 mol) and potassium carbonate (1.95 g, 0.0195 mol) in 100 ml of water is stirred at room temperature for 4 hours then at 45° C. for 2 hours. The reaction mixture is then cooled to room temperature, treated with charcoal and concentrated to afford a wet off-white solid. This material is recrystallized from ethanol to give 2.27 g (39.5 percent) of product as a white-gray solid: mp 275°-290° C.; IR (KBr) 2730-3600, 1610, 980, 760 cm$^{-1}$; $^1$H NMR (CDCl$_3$) δ 3.5 and 4.35 (2d, 2, CH$_2$), 4.5 (s, 1, H$_6$), 6.8-7.5 (m, 8, Ar—H).

Anal. Calcd. for C$_{15}$H$_{11}$O$_4$K.1/2 H$_2$O: C, 59.4; H, 3.99 Found: C, 59.2; H, 4.5

EXAMPLE 16

Diethanolamine Salt of 12H-Dibenzo[d,g][1,3]dioxocin-6-carboxylic Acid

To a stirred solution of 12H-Dibenzo[d,g][1,3]dioxocin-6-carboxylic acid (4.0 grams, 0.0156 mol) in 40 ml of tetrahydrofuran is added diethanolamine (1.64 grams, 0.0156 mol). After 2 hours at room temperature, the solids that formed are collected by filtration, washed with ether and dried to afford 5.04 grams (89 percent) of product as a white solid: mp 114°-116° C.; IR (KBr) 3.0-4.0, 6.25, 6.79, 7.05, 8.1, 10.35 cm$^{-1}$; $^1$H NMR (60 MHz, DMSO-d$_6$) δ 3.05 (m, 4, (CH$_2$CH$_2$OH)$_2$), 3.55 and 4.37 (2d, 2, CH$_2$), 3.75 (m, 4, (CH$_2$CH$_2$OH)$_2$), 4.69 (s, 1,CH), 6.4-7.5 (m, 12, Ar—H and 4 exchangeable).

Anal. Calcd. for C$_{19}$H$_{23}$O$_6$: C, 63.15; H, 6.41; N, 3.88 Found: C, 63.2; H, 6.4; N, 4.0

EXAMPLE 17

12H-Dibenzo[d,g][1,3]dioxocin-6-carboxylic acid dimethylamine salt

To a solution of 12H-dibenzo[d,g][1,3]dioxocin-6-carboxylic acid (5 g, 19.5 mmol) in ethyl acetate/benzene is added excess liquid dimethylamine at 0° C. under nitrogen. The mixture is stirred overnight at room temperature under nitrogen. The resultant solid is filtered and dried to yield 5.5 g of white solid, mp 164°-172° C.: IR (KBr) 1640 cm$^{-1}$; $^1$H NMR (CDCl$_3$) δ 2.51 (s, 6H, NCH$_3$), 3.47, 3.6, 4.25, and 4.4 (q, 2H, CH$_2$), 4.55 (s, 1H, CHCO$_2$) 6.8–7.5 (m, 8H, aromatic).

Anal. Calcd., for C$_{17}$H$_{19}$O$_4$N: C, 67.76; H, 6.36; N, 4.65 Found: C, 67.7; H, 6.5; N, 5.0

EXAMPLE 18

4(2,2-Dimethyl-1,3-dioxolanyl)methyl 12H-dibenzo[d,g][1,3]dioxocin-6-carboxylate 12H-Dibenzo[d,g][1,3]dioxocin-6-carbonyl chloride (10 g, 39 ;mmol) is dissolved in toluene and added to a solution of glycerolketal (5.6 ml, 45 mmol) and 10 ml of triethylamine in toluene at 0°–10° C. under argon. The mixture is heated at reflux for 5 hours, cooled to room temperature, poured into 150 ml of water and extracted with 4×150 ml of ethyl acetate. The organic solution is washed with 5 percent HCl, 5 percent NaOH and then brine, dried with magnesium sulfate and filtered The solvent is removed and the residue chromatographed on dry column silica gel using ethyl ether/hexane (1:1) as the solvent to give a yellowish liquid which is crystallized in petroleum ether. The solid is filtered and washed with petroleum ether to give a white solid, mp 109°–111° C.: IR (KBr) 1780, 1581 cm$^{-1}$, $^1$H NMR (CDCl$_3$) δ 1.4 and 1.47 (2S, 6H, CH$_3$), 3.36, 3.58, 4.49 and 4.7 (q, 2H, CH$_2$), 3.7–4.4 (m, 3H, CHO and CH$_2$O), 4.4–4.6 (m, 2H, OCH$_2$), 5.1 (s, 1H, OCHO), 6.95–7.45 (m, 8H, aromatic).

Anal. Calcd. for C$_{21}$H$_{22}$O$_6$: C, 68.10; H, 5.99 Found: C, 68.3; H, 6.0

EXAMPLE 19

Methyl-6-Methyl-12H-Dibenzo[d,g][1,3]dioxocin-6-carboxylate

To a stirred solution of isopropyl cyclohexyl amine (2.92 ml, 0.0178 mol) in 15 ml of dry tetrahydrofuran (THF) under N$_2$ at 0° C. is added n-BuLi (11.84 ml of 1.5 M in hexane). After stirring 15 minutes at 0° C., the solution is cooled to −65° C. and a solution of methyl 12H-dibenzo[d,g][1,3]dioxocin-6-carboxylate (4.0 g, 0.0148 mol) in 10 ml of THF is added dropwise over a period of 5 minutes. The solution is stirred at −65° C. for an additional 10 minutes and then added via syringe over a period of 2 minutes to a solution of methyl iodide (1.84 ml, 0.0246 mol) in 25 ml of dry dimethyl sulfoxide at room temperature After stirring for 30 minutes, the reaction mixture is diluted with 300 ml of CH$_2$Cl$_2$, washed with H$_2$O, 1N HCl and then brine, dried over MgSO$_4$ and concentrated. The residue obtained is purified by dry column chromatography (elution with 1:4 ethyl acetate-hexanes) to afford 2 g of a yellow syrup. This material was subjected to HPLC purification (Waters 500, 2 columns, 4 cycles, elution with 1:7 ethylacetatehexanes) to afford 1.1 g (26 percent) of product as a clear sirup: IR (neat) 5.65, 6.3, 6.7, 6.85, 7.25 cm$^{-1}$; $^1$H NMR (60 MHz, CDCl$_3$) δ 1.36 (s, 3, CH$_3$), 3.71 and 4.32 (2d, 2, CH$_2$) 3.9 (s, 3, OCH$_3$), 6.95–7.4 (m, 8, Ar—H).

Anal. Calcd. for C$_{17}$H$_{16}$O$_4$: C, 71.82; H, 5.67 Found: C, 71.8; H, 5.7

EXAMPLE 20

(cis and trans)
Methyl-12-Methyl-12H-Dibenzo[d,g][1,3]dioxocin-6-carboxylate

A mixture of 2,2′ethylidenebisphenol (10.0 grams, 0.0467 mol), dichloroacetic acid (3.85 ml, 0.0467 mol) and potassium carbonate (25.8 grams, 0.187 mol) in 200 ml of isopropyl alcohol is heated at reflux for 24 hours with vigorous stirring, after which an additional 3.85 ml of dichloroacetic acid is added and the mixture refluxed with stirring for 70 hours. The isopropyl alcohol is removed by distillation at atmospheric pressure and replaced gradually with H$_2$O. The reaction mixture is cooled, acidified by addition of concentrated HCl and extracted into chloroform. The chloroform extract is washed with brine, treated with charcoal, dried over MgSO$_4$ and concentrated to afford a quantitative yield of crude acid. This material is then converted to the methyl ester by refluxing in a methanol solution (100 ml) in the presence of conc. H$_2$SO$_4$ (0.6 ml) for 2 hours. The solution is cooled, 50 ml of CH$_2$Cl$_2$ is added and the mixture neutralized by the addition of solid Na$_2$CO$_3$. The inorganic salts are removed by filtration and the filtrate concentrated and taken up into CH$_2$Cl$_2$, washed with brine, dried over MgSO$_4$ and concentrated to afford 11.5 grams of a dark semi-solid. Dry column chromatography (elution with 1:4 EtOAc-hexane) yields 5.0 grams (38 percent) of product as a white solid consisting of a 1:1 mixture of cis and trans isomers: mp 95°–120° C.; IR (thin film) 5.62, 6.7, 6.9, 8.2, 9.25, 10.05, 13.05 cm$^{-1}$; $^1$H NMR (60 MHz, CDCl$_3$) δ 1.66 and 1.89 (2d, 2, CH$_3$), 3.88 and 3.95 (2s, 3, OCH$_3$), 3.95 and 5.1 (2q, 2, CH), 5.0 and 5.36 (2s, 1, CH), 7.0–7.5 (m, 8, Ar—H).

Anal. Calcd. for C$_{17}$H$_{16}$O$_4$: C, 71.82; H, 5.67 Found: C, 71.6; H, 5.7

EXAMPLE 21

Ethyl 12,12-Dimethyl-12H-dibenzo[d,g][1,3]dioxocin-6-carboxylate

A mixture of 2,2′-isopropylidene bisphenol (3.65 g, 0.01594 mol), potassium hydroxide (2.68 g of 85 percent, 0.0478 mol) and dichloroacetic acid (1.31 ml, 0.01594 mol) in 65 ml cf isopropyl alcohol is heated at reflux. After 20 hours at reflux, an additional 1.79 g of 85 percent KOH and 1.31 ml of dichloroacetic acid are added and the reaction mixture is heated at reflux for 2 days. The reaction mixture is then diluted with 200 ml of H$_2$O, acidified by the addition of concentrated HCl (10 ml) and extracted into ethyl acetate. The ethyl acetate solution is washed with brine, dried over MgSO$_4$ and concentrated. The residue is washed with petroleum ether to afford 3.7 g of crude product as a red-brown syrup. This material is then purified by an esterification-saponification-esterification procedure (esterification agent methanol, H$_2$SO$_4$). Dry column chromatography yields 0.97 g of crude product, which is saponified (NaOH, MeOH-H$_2$O ), and purified by dry column chromatography to afford 0.60 g of a white solid. Esterification of this material (EtOH, H$_2$SO$_4$) and purification by preparative thin layer chromatography (elution with 1:4 ethyl acetate-hexanes) yields 0.25 g of product as a clear syrup: IR (neat) 3.34, 5.65, 6.95, 8.2, 13.2 cm−1; $^1$H NMR (CDCl$_3$) δ1.28 (t, 3, CH$_2\overline{\text{CH}}_3$), 1.75 and 1.9 (2s, 6, (CH$_3$)$_2$C), 4.24 (q, 2 $\overline{\text{CH}}_2$CH$_3$), (s, 1, CH), 6.9–7.6 (m, 8, Ar—H); m/e 312.

Anal. Calcd. for C$_{19}$H$_{20}$O$_4$: C, 73.06; H, 6.45 Found: C, 72.4; H, 5.7

EXAMPLE 22

12H-Dibenzo[d,g][1,3]dioxocin-12-hydroxy-6-carboxylic acid Lactone

To a stirred solution of 12H-dibenzo[d,g][1,3]dioxocin-12-keto-6-carboxylic acid (10.0 g, 0.0370 mol) and sodium hydroxide (1.63 g, 0.0407 mol) in 200 ml of 5:3 ethanol-water is added sodium borohydride (1.40 g, 0.0370 mol) and the reaction is heated to 55° C. After 16 hours at 55° C., the reaction is cooled to room temperature and poured cautiously onto 1 HCl (500 ml), then extracted with ethyl acetate. The ethyl acetate solution is washed with brine, dried over $MgSO_4$ and concentrated to afford a quantitative yield of a mixture of alcohols and lactone. This mixture and p-toluenesulfonic acid (0.05 g) in 250 ml of benzene is heated at reflux After 2 hours, the reaction is cooled to room temperature, diluted with ethyl acetate and filtered to remove insoluble polymeric material. The filtrate is washed with saturated aqueous $NaHCO_3$, then brine, dried over $MgSO_4$ and concentrated to afford 6.1 g (64 percent) of a white solid (approximately 95 percent pure). Analytically pure material is obtained by dry column chromatography (elution with 1:2 EtOAc-hexanes), followed by recrystallization from benzene-hexanes: mp 147°–149° C.; IR (KBr) 5.73, 6.74, 7.76, 8.41, 9.74, 13.36 cm$^{-1}$, $^1$H NMR (60 MHZ, CDCl$_3$) δ 5.97 (s, 1, $CHCO_2$-), 6.39 (s, 1, $Ar_2\underline{CH}$—0), 6.8–7.4 (m, 8, Ar—$\underline{H}$).

Anal. Calcd. for $C_{15}H_{10}O_4$: C, 70.86; H 3.96 Found: C, 71.2; H, 4.0

EXAMPLE 23

Ethyl 1-Methyl 12H-dibenzo[d,g][1,3]dioxocin-6-carboxylate

A mixture of 6-methyl-2,2'-methylene bisphenol (3.1 g, 0.0145 mole), potassium hydroxide (2.87 g of 85 percent, 0.0434 mol) and dichloroacetic acid (1.2 ml, 0.0145 mol) in 55 ml of isopropyl alcohol is heated at reflux. After 22 hours at reflux, an additional 1.91 g of 85 percent KOH and 1.2 ml of dichloroacetic acid are added and the reaction mixture is refluxed for 4 hours. The reaction mixture is then cooled, diluted with 150 ml of H$_2$O, acidified by the addition of concentrated HCl and extracted into ethyl acetate. The ethyl acetate solution is washed with brine, dried over $MgSO_4$ and concentrated to afford the crude acid as a gummy yellow-tan solid A solution of the crude acid and concentrated H$_2$SO$_4$ (0.2 ml) in 25 ml of ethanol is heated at reflux After 2 hours the solution is cooled to room temperature, diluted with CH$_2$Cl$_2$ (15 ml) and neutralized by the addition of solid Na$_2$CO$_3$. The inorganics are removed by filtration and the filtrate is concentrated under reduced pressure. The residue obtained is taken up into ethyl acetate, washed with H$_2$O, then brine, dried over $MgSO_4$ and concentrated to afford 3.9 g of an amber syrup. Dry column chromatography (elution with 1:4 ethyl acetate-hexanes) followed by recrystallization from cyclohexane yields 1.0 g of product as a white solid: mp 78°–83° C.; IR (KBr) 1759, 1205, 1065, 980 cm$^{-1}$; $^1$H NMR (CDCl$_3$) δ 1.41 (t, 3, CH$_2$CH$_3$), 2.52 (s, 3, CH$_3$), 3.69 and 4.45 (2d, 2, (AR)$_2$—CH2), 4.4 (q, 2, CH$_2$CH$_3$), 5.05 (s, 1 CH), 6.85–7.5 (m, 7, Ar—H); mass spectrum, m/e (M+) 298.

EXAMPLE 24

Methyl 2-Methyl-12H-dibenzo[d,g][1,3]dioxocin-6-carboxylate

Into a 3-neck round bottom flask fitted with a mechanical stirrer and a condenser, is placed 4-methyl bis (1-hydroxy-2-phenyl)-methane (10.2 g, 48 mmol) and potassium carbonate (26.33 g, 190 mmol) in 200 ml of isopropanol. Dichloroacetic acid (3.93 ml, 48 mmol) is then added and the mixture is heated at reflux for 1 day. More dichloroacetic acid (3.93 ml, 48 mmol) is added and reflux is resumed for 3 more days. 400 ml of water is then added and the mixture is acidified with hydrochloric acid. After stirring the mixture for 2 hours at room temperature and extracting with 200 ml of ethyl acetate twice, the combined organic layer is next washed with 200 ml of IM HCl and 150 ml of brine, dried with magnesium sulfate and filtered The solvent is removed, yielding about 17 g of brown oil. This oil is used directly for esterification. It is dissolved in 150 ml of methanol and 0.3 ml of concentrated sulfuric acid is added. The mixture is heated to reflux for 2 hours and then cooled to room temperature. Sodium carbonate is added and the mixture is stirred for ½ hour. Following filtration of the mixture, the solvent is removed and the crude solids dissolved in methylene chloride, washed with 100 ml of 5 percent sodium hydroxide and 150 ml of brine, dried with $MgSO_4$ and filtered. The solvent is then removed to yield about 7 g of brown solid, which is chromatographed on dry column silica gel using ethyl ether/hexane as the solvent to give about 5.5 g of white solid. This solid was re-crystallized in ethyl ether/hexane to give 4.51 g of white solid. mp 106–108.5° C. IR (KBr): 1761, 1748 cm$^{-1}$. $^1$H NMR (CDCl$_3$): 2.27 (s, 3H, CH$_3$), 3.3, 3.5, 4.46 and 4.67 (q, 2H, CH), 3.92 (s, 3H, OCH$_3$), 5.02 (s, 1H, CHO), 6.85–7.5 (m, 7H aromatic H).

Anal. Calcd. for $C_{17}H_{16}H_4$: C, 71.82, H, 5.67 Found: C, 71.5; H, 5.7

EXAMPLE 25

3-Methyl-12-H-dibenzo[d,g][1,3]dioxocin-6-carboxylic acid

To a suspension of sodium hydride (5.7 g of a 50 percent dispersion in oil, washed with petroleum ether; 0.1193 mol) and 18-crown-6 (0.45 g) in 65 ml of 1,4-dioxane is added slowly, dropwise, a solution of dichloroacetic acid (4.0 ml, 0.049 mol) in 65 ml of 1,4-dioxane over a period of 15 minutes, followed by the dropwise addition of 5-methyl-2,2'methylenebisphenol (6.36 g, 0.0297 mol) in 85 ml of 1,4-dioxane over a period of 45 minutes. The reaction mix is then heated at about 90° C. for 18 hours and then at reflux for 4 hours. Next, it is cooled to room temperature, poured onto 600 ml of H$_2$O, acidified by the addition of concentrated HCl and extracted with ethyl acetate (2×500 ml). The ethyl acetate extract is washed with brine, dried over $MgSO_4$ and concentrated to afford 9.9 g of crude product as a semi-solid. Purification via extraction with cyclohexane in a Soxhlet apparatus yields 5.0 g (62.3 percent) of product as a white solid: mp 149°–152° C.; IR (KBr) 1730, 1245, 1220, 1015 cm$^{-1}$; $^1$H NMR (DMSO-d$_6$) δ 2.2 (s, 3, CH$_3$), 3.54 and 4.3 (2d, 2, h$_{12a}$+H$_{12b}$), 5.01 (s, 1, H$_6$), 6.8–7.5 (m, 7, Ar—H).

Anal. Calcd. for $C_{16}H_{14}O_4$: C, 70.7; H, 5.3 Found: C, 71.1; H, 5.22

EXAMPLE 26

Methyl 4-methyl-12H-dibenzo[d,g][1,3]dioxocin-6-carboxylate

A mixture of crude 6-methyl 2,2'-methylene bisphenol (7.0 g, 0.0327 mol), potassium hydroxide (5.5 g, 0.098 mol) and dichloroacetic acid (2.7 ml, 0.0327 mol) in 130 ml of isopropyl alcohol is heated at reflux for 23 hours, following which an additional 5.5 g of potassium hydroxide (0.098 mol) and then 2 7 ml of dichloroacetic acid (0.0327 mol) are added and the reaction mixture is again heated at reflux for an additional 3 hours. The mixture is then cooled to room temperature, diluted with 400 ml of water, acidified by the addition of concentrated HCl (15 ml), extracted with ethyl acetate (200 ml) and the resultant organic solution is washed with brine, dried over MgSO$_4$ and concentrated. The residue is then co-evaporated with toluene to afford 10 g of crude acid as a tan solid. A solution of the crude acid and concentrated H$_2$SO$_4$ (0.6 ml) in 100 ml cf methanol is heated at reflux for 2 hours, after which the reaction mixture is cooled to room temperature, diluted with 25 ml of CH$_2$Cl and neutralized by the addition of solid Na$_2$CO$_3$ The inorganic salts are removed by filtration and the filtrate concentrated under reduced pressure. The residue is taken up into a mixture of EtOAc-ether, washed with water, 5 percent aqueous NaOH, then brine, dried over MgSO$_4$ and concentrated to afford 7.0 g of a yellow syrup. Dry column chromatography (elution with 1:4 EtOAc-hexanes) afforded 4.1 g (44 percent) of product as a white solid; greater than 95 percent purity. Recrystallization from cyclohexane afforded 2 1 g (23 percent) of pure product: mp 107°–109°; IR (KBr) 5.74 6.97, 8.3, 9.5, 10.2, 13.5 cm$^{-1}$; $^1$H NMR (90 MHz, CDCl$_3$) δ, 2.23 (s, 3, CH$_3$), 3.41 (d, 1, H-C$\underline{\text{H}}$), 3.95 (s, 3, OCH$_3$), 4.62 (d, 1, $\underline{\text{H}}$ C-H), 5.04 (s, 1, OC$\overline{\text{H}}$O), 6.9–7.4 (m, 7, Ar—H).

Anal. Calcd. for C$_{17}$H$_{16}$O$_4$: C, 71.82; H, 5.67 Found: C, 71.8; H, 5.6

EXAMPLE 27

2-Methoxyethyl 12H-Dibenzo[d,g][1,3]dioxocin-6-carboxylate

12H-Dibenzo[d,g][1,3]dioxocin-6-carbonyl chloride (5.33 g, 19.5 mmol) is dissolved in toluene and added to a solution of 2-methoxyethanol (2.2 ml, 27.6 mmol) and 7 ml of triethylamine in toluene at 0°–10° C. under argon. The mixture is heated at reflux for 3 hours, cooled to room temperature, poured into 150 ml of water and extracted with 4×100 ml of ethyl acetate The resultant organic solution is washed with 5 percent hydrochloric acid, 5 percent sodium hydroxide and brine, dried with magnesium sulfate and filtered. The solvent is removed to give a brownish solid which is chromatographed on dry column silica gel, using ethyl ether/hexane (1:1) as the solvent, to give a yellowish oil. This oil is solidified, the solid is filtered and washed with ethyl ether/hexane to yield a white solid: mp 74°–76° C. IR (KBr) 1779, 1581 cm$^{-1}$; $^1$H NMR (CDCl$_3$) δ 3.42 (s, 3H, CH$_3$), 3.3–4.0 (m, 3H, CH and OCH$_2$), 4.35–4.8 (m, 3H, CH and OCH$_2$), 5.1 (s, 1H, OCHO), 6.9–7.45 (m, 8H, aromatic).

Anal. Calcd. for C$_{18}$H$_{18}$O$_5$: C, 68.78; H 5 77 Found: C, 69.1; H, 5.9

EXAMPLE 28

2-Ethylhexyl 12H-Dibenzo[d,g][1,3]dioxocin-6-carboxylate

To a stirred solution of 12H-dibenzo[d,g]dioxocin-6carbonyl chloride (4 g, 0.015 mol) in 45 ml of toluene is added a solution of 2-ethylhexanol (2.28 g, 0.017 mol) and 4 ml of triethylamine in toluene at 0° C. under argon. The mixture is heated at reflux for 2 hours, cooled, washed with 5 percent NaOH and then brine, dried with magnesium sulfate and filtered. The solvent is removed to give a brown liquid which is chromatographed on dry column silica gel using ethyl ether/hexane as the solvent to yield a yellowish oil (4.5 g): IR (neat) 1770, 1580 cm$^{-1}$. $^1$H NMR (CDCl$_3$) 0.5–2.0 (m, 15H, CH and CH$_3$), 3.33, 3.53, 4.48, and 4.68 (q, 2H, CH$_2$), 4.15–4.35 (d, 2H, OCH$_2$), 5.2 (s, 1H, CH), 6.9–7.4 (m, 8H, aromatic).

Anal. Calcd for C$_{23}$H$_{28}$O$_4$: C, 74.97; H, 7.66 Found: C, 75.1, H, 7.9

EXAMPLE 29

Ethyl 3-t-Butyl-12--dibenzo[d,g][1,3]dioxocin-6-carboxylate

A mixture of 4-t-butyl-2,2'-methylene bisphenol (3.67 g, 0.0143 mol), potassium hydroxide (2.84 g of 85 percent, 0.0429 mol) and dichloroacetic acid (1.18 ml, 0.0143 mol) in 55 ml of isopropyl alcohol is heated at reflux. After 17 hours at reflux, an additional 1.90 g of 85 percent KOH and 1.18 ml of dichloroacetic acid is added and reflux is continued for 4 hours. Thereafter, the reaction mixture is cooled to room temperature, diluted with 150 ml of H$_2$O, acidified by the addition of concentrated HCl and extracted into ethyl acetate The ethyl acetate solution is washed with brine, dried over MgSO$_4$ and concentrated to afford crude acid as a yellow-brown syrup. A solution of the crude acid and p-toluene sulfonic acid (0.07 g) in 25 ml of 10:1 CHCl$_3$-ethanol is heated at reflux for 1.5 hours with azetropic removal of water. The solution is then cooled to room temperature, diluted with 50 ml of CHCl$_3$, washed with H$_2$O, 5 percent aqueous NaOH and then brine, dried over MgSO$_4$, and concentrated to afford 3.93 g of a yellow-brown syrup. Dry column chromatography (elution with 1:4 EtOAc-hexanes) yields 2.4 g (49 percent) of product as a cloudy syrup: IR (neat) 2975, 1770, 1755, 1485, 1410, 1260, 76 cm$^{-1}$; $^1$H NMR (CDCl$_3$) δ 1.24 (s, 9, C(CH$_3$)$_3$), 1.43 (t, 3, CH$_2$CH$_3$), 3.43 and 4.51 (2d, 2 AR$_2$CH$_2$), 4.39 (q, 2, CH$_2$C$\overline{\text{H}_3}$), 5.05 (s, 1 CH), 7.0–7.4 (m, 7, Ar—H); mass spectrum, m/e (M+) 340, (M+—CH$_3$) 323, (M+—CH$_3$CH$_2$OH) 294, (M+—C$_4$H$_9$) 283, (M+—CO$_2$Et) 267.

EXAMPLE 30

Ethyl 3-Trifluoromethyl-12H-dibenzo[d,g][1,3]dioxocin-6-carboxylate

To a suspension of sodium hydride (2.55 g of a 50 percent dispersion in oil, washed with petroleum ether, 0.0531 mol) and 18-crown-6 (0.2 g) in 30 ml of 1,4-dioxane is slowly added dropwise, a solution of dichloroacetic acid (1.81 Ml, 0.0219 mol) in 30 ml of 1,4-dioxane over a period of 15 minutes, followed by the dropwise addition of 5-trifluoromethyl-2,2'-methylene bisphenol (3.56 g, 0.0133 mol) in 40 ml of 1,4-dioxane over a period of 45 minutes. The reaction is then heated at reflux for 20 hours, cooled to room temperature, poured into 300 ml of H$_2$O, acidified by the addition of concentrated HCl, and extracted with ethyl acetate (2×200 ml). The ethyl acetate extract is washed with brine, dried over MgSO$_4$ and concentrated to afford an oily residue which is further washed with petroleum ether to give 4.6 g of an orange-yellow semi-solid A solution of this material and p-toluene sulfonic acid (0.07 g) in 30 ml of 10:1 CHCl$_3$-ethanol is heated at reflux for 1 hour with azetropic removal of water. The solution is then cooled to room temperature, diluted with 50 ml of CHCl$_3$, washed with H$_2$O, 5 percent aqueous NaOH, and then brine, dried over MgSO$_4$, and concentrated to afford 3.75 g of a dark residue. Flash chromatography of this material (elution with 1:6 ethyl acetate-hexanes) affords 1.91 g (41 percent) of product as a white solid: mp 78–81° C.; IR (KBr) 1765, 1325, 1115, 990 cm$^{-1}$; $^1$H NMR (CDCl$_3$) δ 1.41 (t, 3, CH$_2$CH$_3$), 3.52 and 4.51 (2 d, 2, H$_{12a}$, H$_{12b}$), 4.41 (q, 2, CH$_2$CH$_3$), 5.09 (s, 1, H$_6$), 7.0–7.5 (m, 7, Ar-H).

Anal Calcd. for C$_{18}$H$_{15}$F$_3$O$_4$: C, 61 37; H, 4.29 Found: C, 61.4; H, 4.2

EXAMPLE 31

Methyl 4,8-Dimethyl 12H-dibenzo[d,g][1,3]dioxocin-6-carboxylate

A mixture of 2,2'-methylene bis-6-methyl phenol (4.0 g, 0.0175 mol), dichloroacetic acid (1.45 ml, 0.0175 mol) and potassium carbonate (9.7 g, 0.070 mol) in 100 ml of isopropyl alcohol is heated at reflux for 24 hours with vigorous stirring after which an additional 1.45 ml of dichloroacetic acid is added and the mixture refluxed with stirring for 70 hours. The isopropyl alcohol is removed by distillation at atmospheric pressure and replaced gradually with H$_2$O. The mixture is cooled to 0° C. and the solids collected by filtration. Water (75 m) is added to the solids and the mixture made strongly acidic with concentrated HCl. The mixture is extracted into CH$_2$Cl$_2$, washed with brine, dried over MgSO$_4$ and concentrated to afford 3.0 g (73 percent) of the carboxylic acid. Esterification (methanol, H$_2$SO$_4$, reflux) followed by dry column chromatography (elution with 1:4 ethyl acetate-hexanes), affords 1.9 g (50 percent) of product as a white solid: mp 134°–135° C.; IR (KBr) 5.65, 6.72, 8.2, 13.1 cm$^{-1}$; $^1$H NMR (60 MHz, CDCl$_3$) δ 2.21 (s, 6, 2 CH$_3$), 3.38 and 4.62 (2d, 2, CH$_2$), 4.0 (s, 3, CH$_3$), 4.99 (s, 1, CH), 6.9–7.3 (m, 6, Ar—H).

Anal. Calcd. for C$_{18}$H$_{18}$O$_4$.1/4H$_2$O: C, 71.4; H, 6.16 Found: C, 71.2; H, 6.1

EXAMPLE 32

Methyl 4,8-Dichloro 12H-dibenzo[d,g][1,3]dioxocin-6-carboxylate

A mixture of 2,2'-methylene bis-6-chlorophenol (10.0 g, 0.0372 mol), dichloroacetic acid (3.07 ml, 0.0372 mol) and potassium carbonate (20.6 g, 0.149 mol) in 150 ml of isopropyl alcohol is heated at reflux for 24 hours with vigorous stirring after which an additional 3.07 ml of dichloroacetic acid is added and the mixture refluxed with stirring for 67 hours. The isopropyl alcohol is removed by distillation at atmospheric pressure and replaced with water, gradually. The reaction mixture is cooled, acidified by addition of concentrated HCl and extracted with CHCl$_3$. The chloroform extract is washed with brine, treated with charcoal, dried over MgSO$_4$ and concentrated to afford 12.3$_g$ of crude carboxylic acid. Esterification (methanol, H$_2$SO$_4$, reflux) followed by dry column chromatography (elution with 1:4 ethyl acetate-hexanes) affords 5.29 g of product as a white solid: mp 114°–116° C.; IR (KBr) 5.65, 6.95, 8.29, 9.47, 10.3 cm$^{-1}$; $^1$H NMR (60 MHz, CDCl$_3$) δ 3.47 and 4.67 (2d, 2, CH$_2$), 3.99 (s, 3, CH$_3$), 5.04 (s, 1, CH), 6.9–7.3 (8, m, Ar—H).

Anal. Calcd. for C$_{16}$H$_{12}$Cl$_2$O$_4$: C, 56.66; H, 3.57 Found: C, 56.7; H, 3.5

EXAMPLE 33

3,9-Dimethyl-12H-dibenzo[d,q][1,3]dioxocin-6-carboxylic acid

A mixture of 2,2'-methylenebis(5-methylphenol) (8.3 g, 0.0364 mol), dichloroacetic acid (3.0 ml, 0.0364 mol) and potassium carbonate (20.1 g, 0.145 mol) in 220 ml of isopropyl alcohol is heated at reflux for 24 hours with vigorous stirring after which an additional 3.0 ml (0.0364 mol) of dichloroacetic acid is added and the mixture is refluxed for an additional 72 hours. The isopropyl alcohol is distilled off and replaced with water. The reaction mixture is then cooled to room temperature and acidified by the addition of concentrated HCl (35 ml). The solids that form are collected by filtration, taken up into ethyl acetate and the ethyl acetate solution is washed with 1N HCl, then brine, dried over MgSO$_4$ and concentrated to afford a quantitative yield of crude product as a tan solid. Extraction of the crude product with hot cyclohexane in a Soxhlet extraction apparatus results in 4.55 g (44 percent) of product as a white solid from the cooled cyclohexane solution. Recrystallization from benzene-hexanes yields an analytically pure material: mp 172°–174° C.; IR (KBr) 3.4 5.8, 8.0, 8.9 cm$^{-1}$; $^1$H NMR (60 MHz, DMSO-d$_6$) δ 2.21 (s 6, 2 CH$_3$), 3.52 (d, 1, H—C—H) 4.23 (d, 1, H—C—H), 6.8–7.4 (6, m, Ar—H).

Anal. Calcd. for C$_{17}$H$_{10}$O$_4$: C, 71.82; H, 5 67 Found: C, 72.1; H, 5.7

EXAMPLE 34

Methyl 3,9-Dimethoxy-12H-dibenzo[d,g][1,3]dioxocin-6-carboxylate

To a solution of potassium hydroxide (1.29 g, 23 mmol) in 100 ml of isopropanol is added 1,1'-methylene bis(4-methoxy-2-phenol) (1.8 g, 6.9 mmol) and then, 0.6 ml of dichloroacetic acid (7.2 mmol). The mixture is heated at reflux overnight. The mixture is then cooled to room temperature and potassium hydroxide (1.29 g, 23 mmol) and dichloroacetic acid (0.6 ml, 7.2 mmol) are added. The mixture is again refluxed overnight. The solvent is removed on a rotavap and water is added The mixture is then acidified with concentrated hydrochloric acid and extracted with ethyl acetate three times The organic layer is washed with brine, dried with magnesium sulfate and filtered. The solvent is removed, leaving a yellow oil. This oil is dissolved in 30 ml of methanol and 1 ml of boron trifluoride etherate is added. The mixture is next stirred at room temperature for 4 hours, poured into saturated aqueous sodium chloride (50 ml) and extracted with ethyl acetate three times. The resulting organic solution is washed with 5 percent sodium hydroxide (50 ml) and brine, dried with magnesium sulfate and filtered. The solvent is removed to leave a yellow oil which is chromatographed on a dry column silica gel using ethyl acetate/hexane (2:1) as the solvent to give a white solid (1.16 g), mp 102°–106° C.: IR (KBr) 1750, 1620, 1505 cm $^{-1}$. $^1$H NMR (CDCl$_3$) δ 3.25, 3.4, 4.31 and 4.45 (q, 2H, CH$_2$), 367 (s, 6H, OCH$_3$), 3.92 (s, 3H, OCH$_3$), 5.06 (s, 2H, OCH), 6.5–7.25 (m, 6H, aromatic).

Anal. Calcd. for C$_{18}$H$_{18}$O$_6$: C, 65.45; H, 5.49 Found: C, 65.2; H, 5.5

EXAMPLE 35

Methyl 4-t-Butyl-12H-dibenzo[d,g][1,3]dioxocin-6-carboxylate

To a suspension of sodium hydride (1.65 g of a 50 percent dispersion in oil, washed with petroleum ether, 0.0343 mol) and 18-crown-6 (0.13 g) in 16 ml of 1,4-dioxane is added slowly, dropwise, a solution of dichloroacetic acid (1.17 ml, 0.0142 mol) in 18 ml of 1,4-dioxane over a period of 15 minutes followed by the dropwise addition of 6-t-butyl-2,2'-methylene bisphenol (2.2g, 0.00858 mol) in 21 ml of 1,4-dioxane over a period of 25 minutes. The reaction mixture is then heated at reflux. After 24 hours at reflux, the reaction mixture is cooled to room temperature, poured into 150 ml of H$_2$O, acidified by the addition of concentrated HCl (10 ml) and extracted with ethyl acetate (2×100 ml). The extract is washed with brine, dried over MgSO$_4$ and concentrated to afford crude carboxylic acid as a yellow-brown syrupy residue. This material is taken up into ether (15 ml) and treated with excess ethereal diazomethane (about 0.6 g in 30 ml of ether). After standing overnight at room temperature, the reaction mixture is evaporated and the residue purified by dry column chromatography (elution with 1:4 EtOAC-hexanes) to afford 0.66 g of slightly impure product. Preparative TLC (elution with 1:10 ether: petroleum ether) yields 0.44 g (16 percent) of pure product as an off white solid: mp 113°–117° C.; IR (KBr) 2950, 1760, 1205 970 cm$^{-1}$; $^1$H NMR (CDCl$_3$) δ 1.3 (s, 9, (CH$_3$)$_3$C), 3.42 and 4.6 (2d, 2 CH$_2$), 3.94 (s, 3, COOCH$_3$), 5.05 (s, 1, CH), 6.97–7.4 (m, 7, Ar—H)

Anal. Calcd. for C$_{20}$H$_{22}$O$_4$: C, 73.6; H, 6.79 Found: C, 73.5; H, 7.0

EXAMPLE 36

4-Methyl-12H-dibenzo[d,g][1,3]dioxocin-6-carboxylic acid, diethanolamine salt A solution of 4-methyl-12H-dibenzo[d,g][1,3]dioxocin-6-carboxylic acid (0.64 g, 0.00237 mol) and diethanolamine (0.25 g, 0.00237 mol) in 6.4 ml of THF is stirred at room temperature After 18 hours, the clear solution is concentrated under reduced pressure and the residue stirred for 1 hour with 15 ml of ether. The ether is then decanted away, leaving a clear syrup which is dried under vacuum to afford 0.88 g (99 percent) of a white hygroscopic crystalline foam: IR (thin film) 3.0, 6.15 8.12, 10.32; $^1$H NMR (CDCl$_3$) δ 2.21 (s, 3, CH$_3$), 3.1–3.5 (m, 5, 2 CH$_2$ and (Ar)$_2$—C—H), 3.8–4.2 (m, 4, 2 CH$_2$), 4.45 (d, 1, (Ar)$_2$—C—H), 4.8 (s, 1, CH), 6.8–7.4 (m, 7, Ar—H)

USE

EXAMPLE 37

Pre and Post Emergent Herbicidal Activity

The herbicide screening test is designed to identify compounds that exhibit pre-emergence (Pre) and/or post-emergence (Post) herbicidal activity. Plantings of the indicated test species are seeded in separate fiber pans (8"×10"×3" deep) containing pasteurized soil. The Post pans are seeded two weeks prior to treatment. The Pre pans are seeded one day prior to application of the test compounds. One Pre and one Post pan is employed for each compound, unless otherwise indicated. Prior to application of the test formulation, the Pre pans are mist watered to stabilize the soil surface. The standard laboratory formulation at the 8 kg/ha treatment rate is prepared by weighing 73.6 mg of the test compound into a 125 ml flask to which is then added 40 ml of acetone followed by 40 ml of 0.1% Ortho X-77 surfactant. If the test compound appears insoluble in the formulation, it is treated for 1–2 minutes with an ultrasonic probe. If still insoluble, the particle size is reduced by grinding to a size sufficient to allow it to pass through the spray nozzle Following preparation of the test formulations, each is then sprayed equally and completely on the Pre and Post pans employing a handheld spray gun with an air atomizing nozzle. Acetone is employed to rinse the spray gun between application of each formulation. The treated pans are then moved to a growth room, or greenhouse, where they are maintained and appropriately watered for 13 days following treatment. At this time, the pans are then evaluated to determine the percent kill/inhibition/ suppression relative to an untreated control. The rating numbers range from 0, indicating no injury, to 100, indicating complete kill or control. Compounds that show 80% control Post and 50% control Pre against any 3 species are considered for further testing. Results are shown in the following Table.

TABLE 1

| COMPOUND | BATCH | TEST TYPE | DOSE KG/HA | PIGWEED | VEL. LEAF | MUSTARD | RED MIL. | FOX TAIL | B.Y. GRSS | JOHNSON | HEMP SESB | MORN GLRY | WILD OATS |
| --- | --- | --- | --- | --- | --- | --- | --- | --- | --- | --- | --- | --- | --- |
| Exp. 1 | 1 | Pre | 8 | 95 | 40 | 95 | 10 | 25 | 60 | 60 | 60 | 45 | 25 |
| | | | 4 | 40 | 60 | 100 | 10 | 20 | 80 | 40 | 70 | 40 | 30 |
| | | | 2 | 40 | 60 | 100 | 10 | 30 | 60 | 20 | 40 | 30 | 20 |
| | | | 1 | 40 | 30 | 100 | 0 | 0 | 30 | 10 | 30 | 20 | 20 |
| | | Post | 8 | 35 | 95 | 100 | 10 | 30 | 35 | 20 | 85 | 70 | 10 |
| | | | 4 | 90 | 25 | 90 | 10 | 10 | 20 | 10 | 100 | 20 | 10 |
| | | | 2 | 70 | 10 | 80 | 0 | 0 | 20 | 10 | 80 | 0 | 0 |
| | | | 1 | 40 | 0 | 70 | 0 | 0 | 10 | 0 | 40 | 0 | 0 |
| | 2 | Pre | 4 | 70 | 50 | 90 | 20 | 60 | 20 | 60 | 40 | 0 | 0 |
| | | | 4 | 100 | 50 | 100 | 20 | 70 | 50 | 70 | 70 | 50 | 50 |
| | | | 2 | 70 | 0 | 80 | 20 | 60 | 20 | 20 | 20 | 0 | 60 |
| | | | 2 | 100 | 20 | 100 | 0 | 50 | 10 | 40 | 30 | 10 | 50 |
| | | | 1 | 50 | 50 | 80 | 10 | 30 | 10 | 0 | 0 | 0 | 20 |
| | | | 1 | 100 | 0 | 90 | 0 | 20 | 10 | 20 | 0 | 0 | 0 |
| | | Post | 4 | 50 | 100 | 100 | 20 | 50 | 20 | 30 | 100 | 0 | 20 |
| | | | 4 | 100 | 100 | 100 | 30 | 60 | 60 | 70 | 100 | 20 | 60 |
| | | | 2 | 50 | 60 | 90 | 10 | 30 | 10 | 20 | 90 | 0 | 20 |
| | | | 2 | 90 | 50 | 100 | 20 | 60 | 30 | 60 | 100 | 10 | 30 |
| | | | 1 | 50 | 60 | 80 | 10 | 20 | 10 | 10 | 80 | 0 | 20 |
| | | | 1 | 60 | 20 | 80 | 30 | 50 | 30 | 60 | 80 | 10 | 60 |
| Exp. 2 | 1 | Pre | 8 | 50 | 30 | 90 | 10 | 20 | 20 | 10 | 20 | 0 | 20 |
| | | | 4 | 10 | 10 | 50 | 10 | 20 | 20 | 10 | 0 | 0 | 0 |
| | | | 2 | 0 | 0 | 50 | 0 | 20 | 30 | 10 | 0 | 0 | 0 |
| | | | 1 | 0 | 0 | 50 | 0 | 0 | 20 | 0 | 0 | 0 | 0 |
| | | Post | 8 | 100 | 100 | 100 | 0 | 20 | 30 | 20 | 100 | 30 | 40 |
| | | | 4 | 70 | 100 | 100 | 10 | 30 | 20 | 30 | 100 | 0 | 30 |
| | | | 2 | 40 | 90 | 80 | 0 | 20 | 20 | 0 | 40 | 0 | 20 |
| | | | 1 | 30 | 60 | 40 | 0 | 10 | 10 | 0 | 40 | 0 | 20 |

TABLE 1-continued

| COMPOUND | BATCH | TEST TYPE | DOSE KG/HA | PIG-WEED | VEL. LEAF | MUS-TARD | RED MIL. | FOX TAIL | B.Y. GRSS | JOHN SON | HEMP SESB | MORN GLRY | WILD OATS |
|---|---|---|---|---|---|---|---|---|---|---|---|---|---|
| | 2 | Pre | 4 | 90 | 50 | 100 | 0 | 60 | 80 | 70 | 50 | 30 | 50 |
| | | | 2 | 90 | 10 | 100 | 0 | 50 | 60 | 50 | 50 | 0 | 50 |
| | | | 1 | 90 | 0 | 90 | 0 | 20 | 30 | 30 | 30 | 0 | 0 |
| | | Post | 4 | 80 | 100 | 90 | 10 | 50 | 50 | 60 | 100 | 10 | 60 |
| | | | 2 | 20 | 50 | 50 | 10 | 10 | 50 | 20 | 60 | 0 | 20 |
| | | | 1 | 50 | 30 | 50 | 0 | 0 | 50 | 10 | 30 | 0 | 20 |
| Exp. 3 | 1 | Pre | 8 | 50 | 40 | 100 | 20 | 70 | 70 | 50 | 30 | 20 | 20 |
| | | | 4 | 30 | 10 | 100 | 0 | 40 | 30 | 10 | 0 | 0 | 10 |
| | | | 4 | 50 | 90 | 100 | 10 | 70 | 10 | 70 | 20 | 20 | 0 |
| | | | 2 | 20 | 0 | 50 | 0 | 20 | 20 | 10 | 0 | 0 | 0 |
| | | | 2 | 50 | 0 | 80 | 0 | 50 | 10 | 70 | 20 | 0 | 0 |
| | | | 1 | 0 | 10 | 30 | 0 | 10 | 20 | 0 | 0 | 0 | 0 |
| | | | 1 | 30 | 0 | 80 | 0 | 20 | 0 | 40 | 0 | 0 | 30 |
| | | Post | 8 | 95 | 100 | 100 | 10 | 10 | 30 | 10 | 100 | 20 | 20 |
| | | | 4 | 60 | 100 | 90 | 20 | 10 | 10 | 10 | 100 | 30 | 10 |
| | | | 4 | 100 | 100 | 100 | 50 | 60 | 60 | 70 | 100 | 40 | 60 |
| | | | 2 | 60 | 50 | 90 | 10 | 10 | 0 | 10 | 80 | 30 | 10 |
| | | | 2 | 100 | 100 | 100 | 20 | 60 | 40 | 60 | 100 | 20 | 30 |
| | | | 1 | 50 | 40 | 90 | 10 | 10 | 20 | 0 | 70 | 0 | 0 |
| | | | 1 | 50 | 90 | 80 | 0 | 30 | 0 | 20 | 100 | 10 | 20 |
| Exp. 4 | 1 | Pre | 8 | 100 | 95 | 100 | 35 | 70 | 90 | 100 | 60 | 80 | — |
| | | | 4 | 95 | 45 | 100 | 50 | 55 | 70 | 70 | 60 | 50 | — |
| | | | 2 | 90 | 15 | 95 | 35 | 20 | 80 | 50 | 20 | 50 | — |
| | | | 1 | 90 | 0 | 90 | 30 | 35 | 50 | 50 | 20 | 20 | — |
| | | Post | 8 | — | 100 | 100 | 25 | 45 | 80 | 95 | 100 | 75 | — |
| | | | 4 | 80 | 90 | 90 | 55 | 70 | 80 | 65 | 95 | 65 | — |
| | | | 2 | 75 | 80 | 80 | 35 | 50 | 60 | 55 | 80 | 50 | — |
| | | | 1 | 50 | 40 | 80 | 15 | 20 | 45 | 20 | 75 | 0 | — |
| | 2 | Pre | 8 | 100 | 40 | 100 | 0 | 20 | 70 | 45 | 60 | 25 | 30 |
| | | | 4 | 85 | 30 | 100 | 0 | 10 | 65 | 40 | 45 | 20 | 25 |
| | | | 2 | 75 | 10 | 90 | 0 | 0 | 45 | 40 | 35 | 20 | 20 |
| | | | 1 | 75 | 10 | 90 | 0 | 0 | 40 | 30 | 30 | 20 | 20 |
| | | Post | 8 | 70 | 100 | 100 | 10 | 10 | 25 | 25 | 95 | 0 | 10 |
| | | | 4 | 95 | 100 | 100 | 0 | 0 | 20 | 25 | 95 | 0 | 0 |
| | | | 2 | 90 | 90 | 95 | 0 | 0 | 10 | 10 | 85 | 0 | 0 |
| | | | 1 | 90 | 90 | 95 | 0 | 0 | 10 | 10 | 85 | 0 | 0 |
| Exp. 5 | 1 | Pre | 8 | 20 | 20 | 70 | 0 | 20 | 60 | 20 | 10 | 0 | 20 |
| | | | 4 | 20 | 10 | 50 | 0 | 20 | 20 | 30 | 10 | 0 | 0 |
| | | | 2 | 20 | 0 | 40 | 0 | 10 | 20 | 0 | 0 | 0 | 0 |
| | | | 1 | 10 | 0 | 30 | 0 | 0 | 20 | 0 | 0 | 0 | 0 |
| | | Post | 8 | 70 | 90 | 90 | 10 | 20 | 30 | 20 | 100 | 20 | 20 |
| | | | 4 | 90 | 90 | 100 | 20 | 20 | 20 | 30 | 100 | 30 | 20 |
| | | | 2 | 100 | 100 | 100 | 10 | 20 | 20 | 30 | 100 | 0 | 10 |
| | | | 1 | 30 | 40 | 100 | 0 | 0 | 0 | 0 | 80 | 0 | 10 |
| Exp. 6 | 1 | Pre | 8 | 50 | 40 | 90 | 0 | 50 | 60 | 50 | 20 | 20 | 20 |
| | | | 4 | 20 | 10 | 50 | 0 | 30 | 30 | 10 | 0 | 0 | 0 |
| | | | 2 | 10 | 0 | 50 | 0 | 30 | 20 | 0 | 20 | 0 | 0 |
| | | | 1 | 0 | 0 | 40 | 0 | 20 | 20 | 0 | 0 | 0 | 0 |
| | | Post | 8 | 70 | 100 | 80 | 20 | 20 | 20 | 20 | 90 | 30 | 20 |
| | | | 4 | 80 | 100 | 100 | 10 | 10 | 10 | 0 | 70 | 0 | 0 |
| | | | 2 | 70 | 100 | 40 | 0 | 10 | 10 | 0 | 70 | 0 | 0 |
| | | | 1 | 20 | 0 | 20 | 0 | 0 | 10 | 0 | 20 | 0 | 0 |
| Exp. 7 | 1 | Pre | 8 | 50 | 30 | 60 | 0 | 80 | 40 | 20 | 0 | 0 | 10 |
| | | | 4 | 40 | 20 | 20 | 0 | 50 | 40 | 40 | 0 | 0 | 20 |
| | | | 2 | 20 | 0 | 0 | 0 | 50 | 30 | 20 | 0 | 0 | 10 |
| | | | 1 | 20 | 0 | 0 | 0 | 40 | 30 | 20 | 0 | 0 | 10 |
| | | Post | 8 | 40 | 80 | 80 | 20 | 20 | 30 | 30 | 90 | 20 | 0 |
| | | | 4 | 100 | 100 | 90 | 0 | 30 | 40 | 20 | 80 | 20 | 0 |
| | | | 2 | 90 | 100 | 80 | 0 | 20 | 20 | 20 | 50 | 0 | 0 |
| | | | 1 | 40 | 60 | 40 | 0 | 10 | 10 | 10 | 40 | 0 | 0 |
| Exp. 8 | 1 | Pre | 8 | 30 | 10 | 95 | 0 | 0 | 80 | 85 | 45 | 35 | 50 |
| | | | 4 | 40 | 0 | 100 | 0 | 0 | 40 | 80 | 30 | 0 | 40 |
| | | | 2 | 0 | 0 | 90 | 0 | 0 | 35 | 40 | 25 | 0 | 10 |
| | | | 1 | 0 | 0 | 80 | 0 | 0 | 10 | 10 | 0 | 0 | 0 |
| | 1 | Post | 8 | 75 | 80 | 99 | 0 | 0 | 50 | 50 | 95 | 50 | 45 |
| | | | 4 | 95 | 85 | 100 | 10 | 10 | 45 | 80 | 95 | 40 | 40 |
| | | | 2 | 45 | 80 | 95 | 0 | 0 | 45 | 15 | 90 | 30 | 25 |
| | | | 1 | 45 | 30 | 70 | 0 | 0 | 40 | 15 | 25 | 10 | 20 |
| Exp. 9 | 1 | Pre | 4 | 100 | 20 | 90 | 20 | 40 | 30 | 30 | 80 | 80 | 20 |
| | | | 2 | 75 | 0 | 95 | 20 | 30 | 10 | 0 | 40 | 40 | 20 |
| | | | 1 | 50 | 0 | 60 | 0 | 0 | 0 | 20 | 30 | 20 | 0 |
| | 1 | Post | 4 | 90 | 70 | 70 | 10 | 20 | 20 | 10 | 60 | 70 | 30 |
| Exp. 10 | 1 | Pre | 4 | 20 | 0 | 40 | 0 | 0 | 0 | 20 | 30 | 0 | 20 |
| | 1 | Post | 4 | 40 | 100 | 85 | 0 | 30 | 30 | 40 | 100 | 40 | 40 |
| | | | 2 | 50 | 0 | 40 | 0 | 0 | 20 | 0 | 40 | 20 | 0 |
| Exp. 11 | 1 | Pre | 4 | 80 | 0 | 60 | 0 | 0 | 0 | 20 | 50 | 30 | 20 |
| | | | 2 | 40 | 0 | 70 | 0 | 20 | 0 | 30 | 40 | 40 | 10 |
| | | | 1 | 40 | 0 | 70 | 0 | 20 | 0 | 30 | 30 | 20 | 10 |
| | 1 | Post | 4 | 80 | 100 | 100 | 0 | 30 | 30 | 40 | 100 | 80 | 30 |
| | | | 2 | 50 | 0 | 80 | 0 | 0 | 10 | 0 | 40 | 0 | 0 |

TABLE 1-continued

| COM-POUND | BATCH | TEST TYPE | DOSE KG/HA | PIG-WEED | VEL. LEAF | MUS-TARD | RED MIL. | FOX TAIL | B.Y. GRSS | JOHN SON | HEMP SESB | MORN GLRY | WILD OATS |
|---|---|---|---|---|---|---|---|---|---|---|---|---|---|
| | | | 1 | 0 | 0 | 40 | 0 | 0 | 0 | 0 | 20 | 0 | 0 |
| Exp. 12 | 1 | Pre | 8 | 80 | 70 | 90 | 20 | 80 | 70 | 70 | 70 | 30 | 70 |
| | | | 4 | 40 | 20 | 80 | 0 | 70 | 80 | 40 | 60 | 30 | 40 |
| | | | 2 | 40 | 10 | 90 | 0 | 60 | 0 | 30 | 70 | 30 | 10 |
| | | | 1 | 30 | 0 | 60 | 0 | 30 | 0 | 10 | 70 | 30 | 10 |
| | | Post | 8 | 20 | 100 | 100 | 20 | 30 | 30 | 40 | 90 | 70 | 50 |
| | | | 4 | 30 | 100 | 80 | 0 | 30 | 0 | 40 | 100 | 20 | 10 |
| | | | 2 | 20 | 100 | 70 | 0 | 0 | 0 | 30 | 100 | 20 | 0 |
| | | | 1 | 40 | 40 | 40 | 0 | 0 | 0 | 10 | 70 | 0 | 0 |
| Exp. 12A | 1 | Pre | 4 | 80 | 40 | 80 | 0 | 40 | 40 | 20 | 50 | 10 | 0 |
| | | | 1 | 20 | 0 | 60 | 0 | 0 | 0 | 0 | 0 | 0 | 0 |
| | | | .25 | 0 | 0 | 40 | 0 | 0 | 0 | 0 | 0 | 0 | 0 |
| | | Post | 4 | 90 | 90 | 100 | 0 | 40 | 40 | 40 | 100 | 80 | 40 |
| | | | 1 | 60 | 2 | 90 | 0 | 20 | 40 | 0 | 80 | 40 | 40 |
| | | | .25 | 20 | 10 | 60 | 0 | 0 | 10 | 0 | 70 | 10 | 10 |
| Exp. 13 | 1 | Pre | 8 | 90 | 80 | 100 | 50 | 70 | 80 | 60 | 60 | 50 | 60 |
| | | | 4 | 100 | 60 | 100 | 60 | 50 | 90 | 80 | 50 | 70 | 60 |
| | | | 2 | 70 | 20 | 80 | 50 | 60 | 60 | 60 | 20 | 10 | 20 |
| | | | 1 | 50 | 0 | 70 | 10 | 50 | 50 | 60 | 10 | 10 | 0 |
| | | Post | 8 | 50 | 100 | 100 | 30 | 50 | 60 | 30 | 70 | 20 | 60 |
| | | | 4 | 60 | 70 | 90 | 50 | 60 | 60 | 40 | 100 | 40 | 50 |
| | | | 2 | 50 | 60 | 80 | 10 | 20 | 30 | 40 | 50 | 20 | 20 |
| | | | 1 | 50 | 40 | 80 | 0 | 10 | 10 | 30 | 50 | 0 | 10 |
| Exp. 14 | 1 | Pre | 8 | 95 | 30 | 95 | 0 | 10 | 70 | 50 | 60 | 35 | 25 |
| | | | 4 | 90 | 70 | 100 | 10 | 20 | 70 | 90 | 90 | 60 | 20 |
| | | | 2 | 90 | 50 | 100 | 0 | 0 | 60 | 60 | 80 | 40 | 20 |
| | | | 1 | 90 | 0 | 100 | 0 | 0 | 40 | 30 | 50 | 40 | 10 |
| | | Post | 8 | 60 | 90 | 45 | 25 | 25 | 20 | 35 | 100 | 0 | 10 |
| | | | 4 | 40 | 10 | 90 | 0 | 10 | 20 | 0 | 70 | 0 | 0 |
| | | | 2 | 30 | 0 | 60 | 0 | 0 | 20 | 0 | 30 | 0 | 0 |
| | | | 1 | 10 | 0 | 60 | 0 | 0 | 10 | 0 | 30 | 0 | 0 |
| Exp. 15 | | | | | | | | | | | | | |
| Exp. 16 | 1 | Pre | 8 | 70 | 25 | 90 | 0 | 20 | 45 | 25 | 40 | 40 | 20 |
| | | | 4 | 90 | 20 | 90 | 0 | 0 | 70 | 20 | 45 | 20 | 20 |
| | | | 2 | 25 | 0 | 70 | 0 | 0 | 40 | 20 | 45 | 20 | 10 |
| | | | 1 | 25 | 0 | 70 | 0 | 0 | 20 | 10 | 30 | 0 | 0 |
| | | Post | 8 | 100 | 70 | 85 | 10 | 10 | 25 | 20 | 45 | 20 | 20 |
| | | | 4 | 100 | 20 | 70 | 0 | 0 | 0 | 0 | 80 | 20 | 0 |
| | | | 2 | 40 | 0 | 45 | 0 | 0 | 0 | 0 | 40 | 10 | 0 |
| | | | 1 | 40 | 0 | 40 | 0 | 0 | 0 | 0 | 40 | 0 | 0 |
| Exp. 17 | 1 | Pre | 4 | 80 | 0 | 70 | 0 | 0 | 0 | 20 | 20 | 0 | 0 |
| | 1 | Post | 4 | 40 | 50 | 100 | 0 | 20 | 0 | 30 | 100 | 20 | 40 |
| Exp. 18 | 1 | Pre | 4 | 70 | 0 | 80 | 0 | 0 | 0 | 10 | 30 | 20 | 0 |
| | | | 2 | 30 | 0 | 30 | 0 | 0 | 0 | 0 | 0 | 0 | 0 |
| | | | 1 | 30 | 0 | 40 | 0 | 0 | 0 | 0 | 30 | 0 | 0 |
| | | Post | 4 | 80 | 95 | 90 | 0 | 40 | 10 | 40 | 95 | 60 | 40 |
| | | | 2 | 20 | 75 | 100 | 0 | 0 | 0 | 20 | 100 | 30 | 20 |
| | | | 1 | 0 | 60 | 90 | 0 | 0 | 0 | 20 | 95 | 20 | 20 |
| Exp. 19 | 1 | Pre | 8 | 90 | 0 | 90 | 0 | 0 | 0 | 0 | 0 | 0 | 0 |
| | 1 | Post | 8 | 90 | 70 | 100 | 0 | 10 | 0 | 20 | 100 | 0 | 0 |
| Exp. 20 | 1 | Pre | 8 | 100 | 80 | 100 | 80 | 90 | 90 | 90 | 80 | 80 | 80 |
| | | | 4 | 100 | 50 | 100 | 50 | 60 | 50 | 80 | 70 | 20 | 60 |
| | | | 2 | 100 | 20 | 100 | 0 | 50 | 60 | 70 | 50 | 0 | 30 |
| | | | 1 | 90 | 0 | 90 | 0 | 20 | 20 | 30 | 0 | 0 | 10 |
| | | Post | 8 | 90 | 70 | 100 | 50 | 60 | 50 | 80 | 100 | 70 | 50 |
| | | | 4 | 100 | 60 | 100 | 30 | 50 | 40 | 60 | 100 | 50 | 60 |
| | | | 2 | 100 | 20 | 100 | 10 | 50 | 60 | 60 | 90 | 20 | 50 |
| | | | 1 | 70 | 10 | 70 | 10 | 30 | 50 | 40 | 80 | 30 | 30 |
| Exp. 21 | 1 | Pre | 4 | 90 | 70 | 80 | 0 | 0 | 0 | 30 | 80 | 20 | 0 |
| | | | 2 | 90 | 40 | 90 | 0 | 20 | 0 | 40 | 50 | 40 | 0 |
| | | | 1 | 60 | 20 | 20 | 0 | 0 | 0 | 20 | 50 | 20 | 0 |
| | 1 | Post | 4 | 100 | 90 | 95 | 0 | 20 | 20 | 50 | 100 | 80 | 30 |
| | | | 2 | 0 | 50 | 70 | 0 | 10 | 30 | 0 | 90 | 30 | 10 |
| | | | 1 | 0 | 50 | 70 | 0 | 0 | 20 | 80 | 30 | 0 | 0 |
| Exp. 22 | 1 | Pre | 8 | 70 | 0 | 90 | 0 | 50 | 0 | 0 | 0 | 0 | 0 |
| | | | 4 | 0 | 0 | 90 | 50 | 60 | 50 | 40 | 0 | 0 | 50 |
| | | | 2 | 0 | 0 | 70 | 40 | 60 | 40 | 20 | 0 | 0 | 30 |
| | | | 1 | 0 | 0 | 50 | 20 | 30 | 20 | 0 | 0 | 0 | 0 |
| | | Post | 8 | 0 | 30 | 60 | 10 | 30 | 20 | 20 | 10 | 30 | 0 |
| Exp. 23 | 1 | Pre | 4 | 0 | 0 | 30 | 0 | 0 | 0 | 0 | 0 | 0 | 0 |
| | | Post | 4 | 50 | 20 | 100 | 0 | 0 | 0 | 0 | 80 | 0 | 0 |
| Exp. 24 | 1 | Pre | 8 | 50 | 40 | 80 | 70 | 70 | 70 | 0 | 70 | 0 | 0 |
| | | | 4 | 60 | 20 | 50 | 20 | 20 | 10 | 0 | 70 | 0 | 30 |
| | | | 2 | 30 | 0 | 40 | 0 | 0 | 0 | 0 | 50 | 0 | 0 |
| | | | 1 | 0 | 0 | 0 | 0 | 0 | 0 | 0 | 0 | 0 | 0 |
| | 1 | Post | 8 | 70 | 30 | 100 | 50 | 60 | 50 | 0 | 80 | 0 | 0 |
| | | | 4 | 0 | 30 | 60 | 10 | 20 | 20 | 0 | 70 | 0 | 0 |
| | | | 2 | 0 | 0 | 60 | 0 | 0 | 0 | 0 | 50 | 0 | 0 |
| | | | 1 | 0 | 0 | 0 | 0 | 0 | 0 | 0 | 0 | 0 | 0 |
| Exp. 25 | 1 | Post | 2 | 90 | 60 | 90 | 0 | 0 | 0 | 0 | 100 | 80 | 0 |

TABLE 1-continued

| COMPOUND | BATCH | TEST TYPE | DOSE KG/HA | PIG-WEED | VEL. LEAF | MUS-TARD | RED MIL. | FOX TAIL | B.Y. GRSS | JOHN SON | HEMP SESB | MORN GLRY | WILD OATS |
|---|---|---|---|---|---|---|---|---|---|---|---|---|---|
| | | | 1 | 80 | 70 | 95 | 0 | 0 | 0 | 0 | 90 | 70 | 0 |
| | | | .50 | 60 | 40 | 90 | 0 | 0 | 0 | 0 | 80 | 40 | 0 |
| Exp. 26 | 1 | Pre | 8 | 70 | 40 | 70 | 20 | 70 | 20 | 50 | 20 | 20 | 40 |
| | | | 4 | 40 | 60 | 70 | 10 | 20 | 60 | 40 | 70 | 40 | 40 |
| | | | 2 | 50 | 40 | 60 | 0 | 30 | 0 | 40 | 30 | 40 | 30 |
| | | | 1 | 40 | 40 | 40 | 0 | 20 | 0 | 30 | 40 | 30 | 0 |
| | 1 | Post | 8 | 10 | 70 | 80 | 10 | 40 | 10 | 40 | 100 | 20 | 20 |
| | | | 4 | 70 | 100 | 100 | 0 | 30 | 10 | 80 | 100 | 80 | 30 |
| | | | 2 | 40 | 100 | 70 | 0 | 0 | 0 | 40 | 100 | 30 | 20 |
| | | | 1 | 70 | 100 | 70 | 0 | 0 | 0 | 30 | 90 | 20 | 30 |
| Exp. 27 | 1 | Pre | 4 | 20 | 30 | 80 | 0 | 10 | 0 | 30 | 60 | 40 | 10 |
| | | | 2 | 50 | 0 | 80 | 0 | 20 | 0 | 40 | 0 | 0 | 10 |
| | | | 1 | 10 | 0 | 60 | 0 | 0 | 0 | 0 | 0 | 0 | 0 |
| | 1 | Post | 4 | 100 | 100 | 100 | 0 | 70 | 40 | 50 | 100 | 85 | 60 |
| | | | 2 | 20 | 70 | 80 | 0 | 0 | 20 | 0 | 40 | 20 | 0 |
| | | | 1 | 0 | 0 | 70 | 0 | 0 | 20 | 0 | 50 | 0 | 0 |
| Exp. 28 | 1 | Pre | 4 | 30 | 0 | 40 | 0 | 0 | 0 | 30 | 50 | 20 | 0 |
| | 1 | Post | 4 | 30 | 50 | 95 | 0 | 40 | 40 | 40 | 100 | 40 | 30 |
| Exp. 29 | 1 | Pre | 4 | 0 | 50 | 0 | 0 | 0 | 0 | 0 | 20 | 0 | 0 |
| | 1 | Post | 4 | 0 | 20 | 90 | 0 | 0 | 0 | 0 | 40 | 40 | 0 |
| Exp. 30 | 1 | Pre | 4 | 40 | 20 | 70 | 0 | 0 | 0 | 0 | 0 | 0 | 0 |
| | 1 | Post | 4 | 90 | 80 | 90 | 0 | 20 | 40 | 50 | 70 | 60 | 40 |
| | | | 2 | 80 | 80 | 95 | 0 | 0 | 40 | 70 | 80 | 70 | 60 |
| | | | 1 | 70 | 40 | 90 | 0 | 0 | 40 | 60 | 80 | 70 | 40 |
| | | | .50 | 20 | 20 | 80 | 0 | 0 | 20 | 20 | 80 | 70 | 20 |
| Exp. 31 | 1 | Pre | 8 | 70 | 60 | 100 | 0 | 0 | 0 | 0 | 50 | 0 | 0 |
| | | | 4 | 80 | 0 | 100 | 0 | 0 | 0 | 0 | 0 | 0 | 0 |
| | | | 2 | 70 | 0 | 90 | 0 | 0 | 0 | 0 | 0 | 0 | 0 |
| | | | 1 | 70 | 0 | 90 | 0 | 0 | 0 | 0 | 0 | 0 | 0 |
| | 1 | Post | 8 | 50 | 60 | 90 | 0 | 0 | 0 | 0 | 70 | 10 | 10 |
| Exp. 32 | 1 | Pre | 8 | 80 | 0 | 80 | 0 | 0 | 0 | 0 | 0 | 0 | 0 |
| | 1 | Post | 8 | 80 | 40 | 90 | 20 | 20 | 10 | 30 | 100 | 30 | 30 |
| | | | 4 | 100 | 70 | 100 | 10 | 10 | 10 | 10 | 100 | 0 | 50 |
| | | | 2 | 80 | 50 | 100 | 0 | 0 | 0 | 0 | 100 | 0 | 50 |
| | | | 1 | 70 | 50 | 100 | 0 | 0 | 0 | 0 | 70 | 0 | 0 |
| Exp. 33 | 1 | Pre | 8 | 100 | 100 | 100 | 50 | 50 | 20 | 20 | 80 | 70 | 0 |
| | | | 4 | 10 | 20 | 70 | 0 | 20 | 0 | 0 | 0 | 0 | 0 |
| | | | 2 | 30 | 20 | 60 | 0 | 0 | 0 | 0 | 20 | 0 | 0 |
| | | | 1 | 0 | 70 | 20 | 0 | 0 | 0 | 0 | 0 | 0 | 0 |
| | | Post | 8 | 90 | 100 | 100 | 20 | 30 | 10 | 30 | 100 | 70 | 0 |
| | | | 4 | 20 | 70 | 100 | 20 | 30 | 20 | 30 | 100 | 20 | 20 |
| | | | 2 | 50 | 80 | 80 | 10 | 20 | 10 | 20 | 80 | 20 | 0 |
| | | | 1 | 50 | 70 | 70 | 10 | 20 | 10 | 10 | 80 | 0 | 10 |
| Exp. 34 | 1 | Pre | 4 | 0 | 0 | 10 | 0 | 0 | 0 | 0 | 0 | 10 | 0 |
| | 1 | Post | 4 | 40 | 80 | 90 | 0 | 0 | 0 | 0 | 90 | 30 | 0 |
| | | | 2 | 0 | 10 | 50 | 0 | 20 | 20 | 0 | 20 | 0 | 10 |
| | | | 1 | 0 | 0 | 60 | 0 | 0 | 0 | 0 | 10 | 0 | 0 |
| Exp. 35 | 1 | Pre | 4 | 0 | 0 | 40 | 0 | 0 | 0 | 0 | 0 | 0 | 0 |
| | 1 | Post | 4 | 0 | 70 | 80 | 0 | 0 | 0 | 0 | 60 | 20 | 60 |
| Exp. 36 | 1 | Pre | 4 | 60 | 0 | 70 | 0 | 10 | 10 | 30 | 50 | 20 | 10 |
| | | | 2 | 30 | 30 | 100 | 0 | 20 | 0 | 60 | 50 | 20 | 30 |
| | | | 1 | 50 | 10 | 70 | 0 | 20 | 0 | 30 | 20 | 0 | 0 |
| | 1 | Post | 4 | 20 | 40 | 90 | 0 | 0 | 0 | 20 | 90 | 40 | 20 |

EXAMPLE 38

Effect on Turf Growth

The acid form of the glyoxylate prepared in Example 1 was evaluated as a turf growth retardant on four grass species at varying rates as indicated in Table 2.

Turf species were planted in 8 by 8 cm fiber pots using steam pasteurized soil, and allowed to grow until well established, i.e., roots extended to the bottom of the fiber pot. The turf was clipped periodically to keep the thatch at a manageable level and fertilizer was applied on a regular basis. Prior to application of the compound to the turf, the grass was cut to one cm. The compound was formulated in 15×125 mm disposable test tubes and foliar applications were made in a hood using a DeVilbliss Model EGA-502 hand held sprayer.

Height measurements were taken two weeks after application of the compound, with the results set forth in Table 2.

TABLE 2

| | HEIGHT* (cm) | | | |
|---|---|---|---|---|
| RATE kg/ha | FESTUCA ARUNDINACEA | POA PRATENSIS | FESTUCA RUBRA | LOLIUM PERENE |
| 0.1 | 5 | 5.5 | 4 | 4 |
| 0.5 | 3 | 3.5 | 3 | 2.5 |
| 1.0 | 2.5 | 3.5 | 3 | 2.5 |
| 2.0 | 2 | 1.5 | 3 | 2 |
| 4.0 | 1 | 1 | 2 | 1.5 |
| Check | 6 | 7 | 4 | 4.5 |

*Average of two replications

Despite some phytotoxicity observed with this method of application, good retardant effect, especially on Kentucky Bluegrass, was demonstrated.

EXAMPLE 39

Effect of Application Method on Turf Retardancy

Using the turf species set forth and grown as in Example 38, the effect of the method of application of the compounds of Examples 16 and 2 is evaluated, with results set forth in Table 3. Weight measurements are taken by cutting each turf pot, after two weeks, to a uniform height, combining the clippings from all species and oven drying prior to weighing.

TABLE 3

| COMPOUND | RATE kg/ha | DRY WEIGHT* (kg/ha) | | |
|---|---|---|---|---|
| | | FOLIAR | SOIL DRENCH | GRANULAR |
| Example 16 | 0.25 | 1.78 | 2.26 | 1.58 |
| | 0.50 | 1.11 | 2.25 | 1.08 |
| | 1.0 | 0.75 | 1.06 | 1.10 |
| | 2.0 | 0.55 | 0.65 | 0.52 |
| | Av. | 1.05 | 1.55 | 1.07 |
| Exampe 2 | 0.25 | 1.10 | 1.51 | 2.44 |
| | 0.50 | 1.45 | 0.83 | 2.48 |
| | 1.0 | 1.12 | 0.72 | 2.10 |
| | 2.0 | 1.20 | 0.32 | 2.03 |
| | Av. | 1.21 | 0.84 | 2.26 |
| Check | — | 2.49 | 2.49 | 2.49 |

*Average of two replications

Granular application is found to result in the lowest degree of phytotoxicity to the grass species.

EXAMPLE 40

Growth Regulation of Wheat

Wheat testing is done in 13 cm round plastic pots. The wheat is planted in a mixture of 75 percent soil and 25 percent sand which has been steam pasteurized to control indigenous weed seed and pathogens. Seeds are planted and then covered with approximately 1 cm soil/sand mix and placed on fiber matting in the greenhouse. The pots are both mist watered and bottom watered until seedlings emerged. After emergence, only bottom watering is done. At the times of treatment, the growth stage is recorded, and pots are removed to a spray hood for treatment. The compound to be applied is placed in a 15 by 125 mm test tube and dissolved in 12 ml of acetone and water. The compound is sprayed onto the foliage using a hand held Devilbiss spray gun (Model EGA-502). This sprayer emits an extremely fine spray particle and results in maximum coverage of the foliage Operating air pressure is 840 gm/cm². Applications are made at four different rates at each of six growth stages. The growth stages are as follows:
I. one leaf
II. three to four leaf, some initial tillering
III. three to four leaf, distinct tillers with two to three leaves
IV. five to six leaf, with four to five tillers
V. flag leaf present, infloresence within culm
VI. boot stage, infloresence emerging from culm Results (being an average of all indicated readings) for the compounds of Examples 1 and 16 are set forth in Tables 4 and 5, respectively.

TABLE 4

EFFECT ON GRAIN WEIGHT, HEIGHT, INTERNODE LENGTH AND BREAKING STRENGTH

| TREATMENT kg/ha | GRAIN WEIGHT gm | PLANT HEIGHT cm | LENGTH cm INTERNODE A | LENGTH cm INTERNODE B | BREAKING STRENGTH gm |
|---|---|---|---|---|---|
| 0 | 0.62 | 38.3 | 24.8 | 8.6 | 61.0 |
| 2 | 0.61 | 31.7 | 19.9 | 7.1 | 66.7 |
| 4 | 0.53 | 31.5 | 20.0 | 7.1 | 53.9 |

*Weight necessary to break a 10 cm segment of Internode A.

TABLE 5

EFFECT ON NUMBER OF TILLERS PRODUCING GRAIN, GRAIN WEIGHT, STRAW WEIGHT AND PLANT HEIGHT

| RATE kg/ha | TILLER COUNT | GRAIN WEIGHT gm | STRAW WEIGHT gm | PLANT HEIGHT cm |
|---|---|---|---|---|
| 0 | 16.2 | 12.1 | 13.4 | 23.3 |
| ½ | 18.1 | 12.6 | 14.7 | 23.7 |
| 1 | 19.0 | 12.8 | 15.2 | 22.5 |
| 2 | 19.7 | 13.7 | 15.8 | 22.9 |
| 4 | 19.2 | 13.1 | 15.0 | 22.9 |

EXAMPLE 41

Effect on Wheat Tillering

Single soft red winter wheat (Triticum aestivum) seedlings growing in soil in 4 inch R plastic pots are treated with broadcast spray applications of the compound of Example 15. At the time of treatment, the plants are starting to tiller Most seedlings have one tiller, while a few have two or no tillers. Treatments are replicated six times (except 5 times at 3 gm/ha). At various times during the course of the study, various parameters are determined: number of flag leaves, number of seed heads and yield measurements. These and other determinations are reported in Table 6. No commercial standard is included, because none is known. The yield increases are attributed to increased tillering (flag leaf counts) and therefore more seed heads per plant. The high dosage (1,000 gm/ha tends to delay tillering.

TABLE 6

| Dosage gm/ha | Number Flag Leaves/Plant | Number Seed Heads/Plant | Total Grain gm (% of control) | Seed Wt. mg/Seed |
|---|---|---|---|---|
| 3 | 6.4 ± 1.5  10.4 ± 3.5 | 10.2 ± 4.1 | 27.1 (136) | 30.4 |
| 10 | 6.0 ± 1.3  8.3 ± 3.1 | 8.2 ± 2.2 | 20.7 (104) | 29.2 |
| 30 | 9.0 ± 2.4  11.7 ± 2.7 | 11.8 ± 3.7 | 28.9 (145) | 28.2 |
| 100 | 7.5 ± 1.5  13.7 ± 2.1 | 14.0 ± 1.7 | 33.5 (168) | 27.7 |
| 300 | 6.0 ± 1.4  13.3 ± 3.3 | 13.5 ± 4.4 | 33.9 (170) | 28.5 |
| 1000 | 3.7 ± 3.1  15.3 ± 2.6 | 14.7 ± 3.3 | 35.0 (176) | 27.9 |
| Control | 5.8 ± 2.5  8.0 ± 3.8 | 7.3 ± 3.4 | 19.9 (100) | 27.0 |

TABLE 6-continued

| Dosage gm/ha | Number Flag Leaves/Plant | Number Seed Heads/Plant | Total Grain gm (% of control) | Seed Wt. mg/Seed |
|---|---|---|---|---|
| DAT[1] | 57 | 96 | 145 (harvest) 162 | 162 |

[1]DAT = Days After Treatment
NOTE:
Grain was pooled for each treatment and weighed 17 days after harvest (162 DAT). The 3 gm/ha treatment was adjusted to 6 replicates.

EXAMPLE 42

Effect on Weed Beets

In some areas where sugar beets (*Beta vulgaris*) are grown, many fields become infested with weed beets which do not form usable roots These weed beets can also bolt any time during the season thus insuring continuing infestations. No herbicide is selective enough to control weed beets in sugar beets A possible weed beet management approach would be to prevent seed production by early treatment of flower stalks with wipe-on or recirculating sprayer applications. To this end, three greenhouse studies are attempted and reported in Table 7. Test plants are grown in 5" R plastic pots. Treatments are applied as directed sprays onto developing flower stalks. Percent reduction is based on fresh weight of surviving floral growth. The compound from Example 1 is prepared as an acetone/water/ surfactant lab formulation. ROUNDUP TM (Monsanto) and A-REST TM (Eli Lilly) are commercial herbicide and plant growth regulant formulations, respectively.

TABLE 7

| Compound | Dosage mg/Plant | Percent Reduction of Floral Parts | | |
|---|---|---|---|---|
| | | Test A | Test B | Test C |
| Example 1 | 0.1 | 16 | 100 | 100 |
| | 0.3 | 35 | 100 | 100 |
| | 0.9 | 100 | 100 | 100 |
| Roundup TM | 2.0 | (56)[2] | 39 | — |
| | 6.0 | 11 | 98 | — |
| | 18.0 | 100 | 100 | — |
| A-Rest TM | 0.33 | — | — | 21 |
| | 1.0 | — | — | 69 |
| | 3.0 | — | — | 92 |
| DAT[1] | | 28 | 63 | 32 |

[1]DAT = Days After Treatment
[2]Denotes percent increase

EXAMPLE 43

Effect on Maple Seedlings

Actively growing seedlings of Acer palmatum (Japanese cutleaf maple) are sprayed to runoff with aqueous dilutions of the compound of Example 15 and ATRINAL TM (a commercial formulation by MAAG of dikegulac). Pinched as well as untreated controls are included All treatments (4 replicates each, recorded 78 days after treatment) are listed in Table 8.

Glyoxylate dosages bracket the range from no effect to an excessive effect at the dosages tested.

TABLE 8

| Compound | Concentration (ppm) | Mean Number Terminals/Plant |
|---|---|---|
| Example 15 | 5 | 1.0 ± 0.0 |
| | 15 | 5.8 ± 2.2 |
| | 50 | 9.5 ± 3.0 |
| | 150 | 9.8 ± 2.4 |
| | 500 | greater than 14 |
| Atrinal | 1500 | 11.5 ± 2.5 |
| | 3000 | 9.0 ± 0.8 |
| Control | — | 1.0 ± 0.0 |

TABLE 8-continued

| Compound | Concentration (ppm) | Mean Number Terminals/Plant |
|---|---|---|
| Pinched Control | — | 1.3 ± 1.5[1] |

[1]Two of the four seedlings went dormant after pinching.

EXAMPLE 44

Effect on Azaleas

Rooted single-stem cuttings of azaleas (Rhododendron sp., cv 'Elsi Lee') are transplanted to artificial potting medium in 4 inch round plastic pots. These cuttings are pinched as they were moved. After growth resumes, these plants are sprayed to run-off using a hand held spray unit. Treatments employ the K salt of Example 15 and dikegulac, a commercial plant growth regulator which is used to induce branching and to prevent regrowth after pruning. Treatments, based on five replicates of each are listed in Table 9.

Flower bud counts are recorded 122 days after treatment. Glyoxylate treatments induced increases in flower bud numbers.

TABLE 9

| Compound | Concentration (ppm) | Mean Number Flower Buds/Plants |
|---|---|---|
| Example 15 | 10 | 3.2 ± 1.9 |
| | 20 | 8.4 ± 3.1 |
| | 40 | 15.8 ± 4.3 |
| | 80 | 23.2 ± 5.8 |
| | 160 | Partial defoliation, Stunted |
| Dikegulac | 1500 | 5.2 ± 3.5 |
| | 3000 | 5.4 ± 2.7 |
| | 6000 | 5.2 ± 3.7 |
| Control | — | 3.0 ± 0.7 |
| Pinched Control* | — | 7.2 ± 2.4 |

*All plants are pinched when potted. The "pinched control" is pinched a second time, when the other plants are sprayed.

What is claimed is:

1. A method of inhibiting the growth of undesirable vegetation which comprises contacting said vegetation's locus with a herbicidally effective amount of a compound having the formula

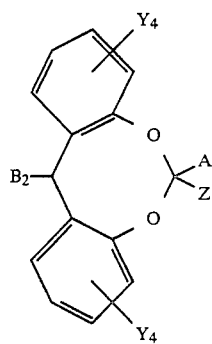

wherein:

A is COOR, COSR, CSNH$_2$, CN or, together with one of B, —C(=O)O—;

R is H, Na, K, di(C$_1$-C$_4$)alkylammonium, diethanolammonium, C$_1$-C$_8$ alkyl, C$_1$-C$_4$ alkoxyalkyl, cyclohexyl, tetrahydrofurfuryl or dimethyldioxolanylmethyl;

Z is H or CH$_3$;

B is H, CH$_3$ or, together with A, —C(=O)O—;

Y is H, C$_1$-C$_4$ alkyl or alkoxy, CF$_3$ or X; and

X is F, Cl or Br, provided that where more than one of Y is other than H on either ring they must be in the 3, 4, 8 and/or 9 positions and, where Y is in the 1, 2, 10 or 11 positions on the rings, no more than one of Y is other than H and that one Y is CH$_3$.

2. A method a in claim 1 wherein Y, B and Z are all H.

3. A method as in claim 1 wherein B and Z are all H.

4. A method as in claim 1 wherein Y and Z are all H.

5. A method as in claim 1 wherein Y at the 1, 2, 10 and 11 positions, B and Z are all H.

* * * * *